United States Patent
Van Der Vliet et al.

(10) Patent No.: US 10,501,541 B2
(45) Date of Patent: Dec. 10, 2019

(54) SINGLE DOMAIN ANTIBODIES TARGETING CD1D

(71) Applicant: LAVA THERAPEUTICS B.V., 's-Hertogenbosch (NL)

(72) Inventors: Johannes Jelle Van Der Vliet, Amsterdam (NL); Tanja Denise De Gruijl, Amsterdam (NL); Hendrik Marinus Willem Verheul, Amsterdam (NL); Renée Cornelia Gerarda De Bruin, Amsterdam (NL); Roeland Lameris, Amsterdam (NL)

(73) Assignee: LAVA THERAPEUTICS B.V., S-Hertogenbosch (NL)

( * ) Notice: Subject to any disclaimer, the term of this patent is extended or adjusted under 35 U.S.C. 154(b) by 0 days.

(21) Appl. No.: 15/546,406

(22) PCT Filed: Jan. 27, 2016

(86) PCT No.: PCT/NL2016/050064
§ 371 (c)(1),
(2) Date: Jul. 26, 2017

(87) PCT Pub. No.: WO2016/122320
PCT Pub. Date: Aug. 4, 2016

(65) Prior Publication Data
US 2018/0142020 A1    May 24, 2018

(30) Foreign Application Priority Data
Jan. 27, 2015    (NL) .................................... 2014192

(51) Int. Cl.
*C07K 16/28* (2006.01)
*C07K 16/30* (2006.01)

(52) U.S. Cl.
CPC ...... *C07K 16/2809* (2013.01); *C07K 16/2833* (2013.01); *C07K 16/30* (2013.01); *C07K 2317/565* (2013.01); *C07K 2317/569* (2013.01); *C07K 2317/75* (2013.01)

(58) Field of Classification Search
None
See application file for complete search history.

(56) References Cited

FOREIGN PATENT DOCUMENTS

| WO | WO 2010130830 | * 11/2010 |
| WO | 2013053021 | 4/2013 |

OTHER PUBLICATIONS

Christina G. Siontorou et al.,"Nanobodies as novel agents for disease diagnosis and therapy", International Journal of Nanomedicine, p. 4215 (Nov. 2013).

Zhao-Hui Ma et al.,"CD1d blockade suppresses the capacity of immature dendritic cells to prime allogeneic T cell response", Journal of Surgical Research, pp. 894-899, vo 1. 183, No. 2 (Feb. 2013).

White et al.,"Antibodies to C0D1d enhance thymic expression of invariant NKT TCR and increase the presence of NOD thymic invariant NKT cells", Developmental and Comparative Immunology, pp. 943-956, vol. 32, No. 8, (Jan. 2008).

Elisa Monzon-Casanov et al., "CD1d Expression in Paneth Cells and Rat Exocrine Pancreas Revealed by Novel Monoclonal Antibodies Which Oifferentially Affect NKT Cell Activation", PLOS One, pp. e1308, vol. 5, No. 9, (Sep. 2010).

Yu et al.,"The diverse functions of CD1d-restricted NKT cells and their potential for immunotherapy", pp. 42-55, vol. 100, No. 1 (Aug. 2005).

S. C. Yue et al.,"Oirect CD1d-Mediated Stimulation of APC IL-12 Production and Protective Immune Response to Virus Infection In Vivo", The Journal of Immunology, pp. 268-276, vol. 184, No. 1 (Nov. 2009).

S. C. Yue et al., "CD1d ligation on human monocytes directly signals rapid NF-B activation and production of bioactive IL-12", Proceedings of the National Acaoemy of Sciences, pp. 11811-11816, vol. 102, No. 1 (Aug. 2005).

Jamie Rossjohn et aL,"Recognition of CD1d-restricted antigens by natural killer T cells,"Nature Reviews Immunology, pp. 845-857, vol. 12, No. 12 (Nov. 2012).

Roelano Lameris et al.,"Exploiting the CD1d-iNKT Cell Axis for Potentiation of OC-Based Cancer Vaccine", Methods in Molecular Biology, pp. 155-165, vol. 1139 (Feb. 2014).

Cecile Vincke et al.,"Introduction to Heavy Chain Antibodies and Derived Nanobodies", Methods in Molecular Biology, pp. 15-26, vol. 911 (Jul. 2012).

Spanoudakis et al., Regulation of multiple myeloma survival and progression by CD1d, Blood, 113(11):2498-2507.

Teng et al., CD1d Activation and Blockade: A New Antitumor Strategy, J Immunol., 182(6):3366-3371 (2009).

Yue et al., Direct CD1d-Mediated Stimulation of APC IL-12 Production and Protective Immune Response to Virus Infection In Vivo, J Immunol., 184(1): 268-276 (2010).

Stirneman et al., Sustained activation and tumor targeting of NKT cells using a CD1d-anti-HER2-scFv fusion protein induce antitumor effects in mice, The Journal of Clinical Investigation, 118(3):994-1005 (2008).

Teng et al., CD1d-Based Combination Therapy Eradicates Established Tumors in Mice, J Immunol., 183(3): 1911-1920 (2009).

* cited by examiner

*Primary Examiner* — Laura B Goddard
(74) *Attorney, Agent, or Firm* — Browdy and Neimark, PLLC

(57) ABSTRACT

The invention relates to compounds, in particular polypeptides that specifically bind to the non-classical MHC protein CD1d and modulate CD1d-mediated biological functions. The invention in particular relates to such compounds and polypeptides comprising or consisting of at least one single domain antibody, and wherein at least one single domain antibody specifically binds to CD1d. Also provided is for methods and use employing such compounds, polypeptides and/or single-domain antibodies.

Figure 1:
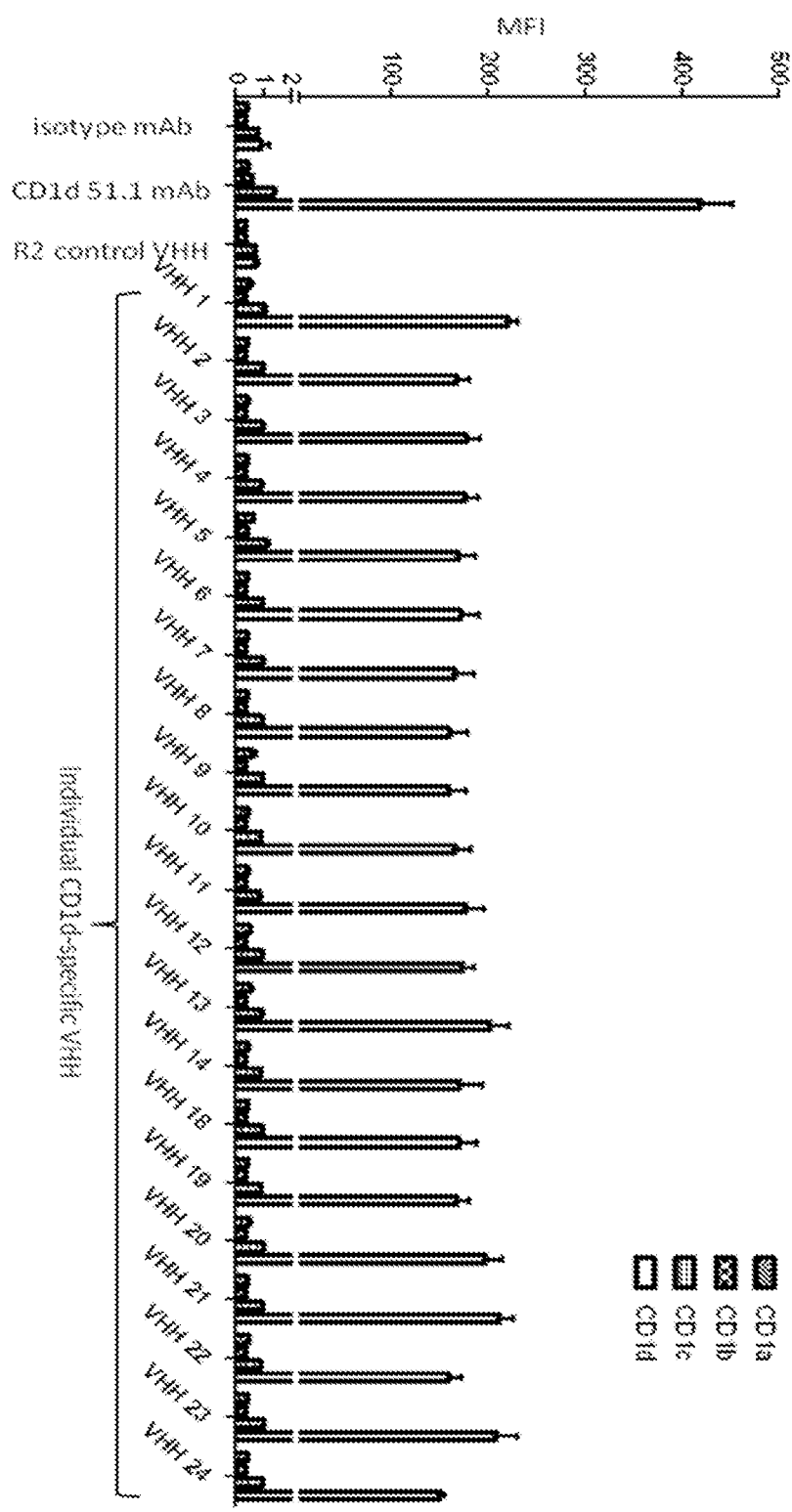

18 Claims, 11 Drawing Sheets
Specification includes a Sequence Listing.

SINGLE DOMAIN ANTIBODIES TARGETING CD1D

The Sequence Listing in ASCII text file format of 40,626 bytes in size, created on Nov. 2, 2017, with the file name "2017-12-11SequenceListing_VANDERVLIET1," filed in the U.S. Patent and Trademark Office on Dec. 11, 2017, is hereby incorporated herein by reference.

FIELD OF INVENTION

The present invention generally relates to the field of immunology, more in particular to the field of single-domain antibodies which bind to human CD1d, including antibodies that modify CD1d-mediated biological functions such as activation of CD1d-restricted T cells, including the natural killer T (NKT) cells, and modulation of the function of cells expressing CD1d. Provided are, for example, compounds which comprise at least one single-domain antibody which binds to CD1d, use of such compounds comprising at least one single-domain antibody and (pharmaceutical) compositions comprising such compounds.

BACKGROUND ART

CD1d is a member of the CD1 (cluster of differentiation 1) family of glycoproteins (including CD1a, CD1b, CD1c, CD1d and CD1e) expressed on the surface of various human cells, including antigen presenting cells (APC). In human CD1d is encoded by CD1D, also known as R3G1. APC displaying CD1d include Langerhans cells, (activated) B-cells, dendritic cells (e.g. in lymph nodes), and (activated) blood monocytes. CD1d is also expressed by various other cell types, for example in liver, pancreas, skin, kidney, uterus, conjunctiva, epididymis, thymus and tonsil (see, for example, Canchis et al. (1992) Immunology 80:561-565).

Cells that are activated/stimulated via CD1d include the Natural Killer T-cells (NKT cells). NKT cells are a heterogeneous group of T cells that share properties of both T cells and natural killer cells. NKT cells are a subset of T cells that express an alpha/beta T-cell receptor (TCR), as well a variety of molecular markers that are typically associated with NKT cells.

Type 1 or invariant NKT cells is the best-known group of NKT cells and differs from conventional αβ T cells in that their T-cell receptors are far more limited in diversity ('invariant'). The NKT cells, including these invariant and other CD1d-restricted T cells (type 2 NKT), recognize (self or foreign) lipids and glycolipids presented by CD1d molecules present on APC. The interaction between (lipid-presenting) CD1d and TCR triggers the release of cytokines including Th1- or Th2-like cytokines, such as interferon-gamma, tumor necrosis factor-alpha, and interleukins like IL-4, IL-5 and IL-13.

Different lipids have been shown to bind CD1d molecules, including mycolic acids, diacylglycerols, and sphingolipids. An alpha-galactosylceramide, KRN7000, is the best studied ligand of the lipid-binding CD1d in NKT cell activation in vitro and in vivo. Other ligands comprise isoglobotrihexosylceramide, (microbial-derived) glycuronosylceramides, alpha-C-galactosylceramides, threitol ceramide, and a variety of (human and non-human) glycolipids such as lysophophatidylcholine and lysosphingomyelin (see, for example, Fox et al (2009) PLOS Biology 7:10: e1000228).

Important roles of NKT cells have now been demonstrated in the regulation of autoimmune, allergic, antimicrobial, and antitumor immune responses (van der Vliet et al. (2004) Clinical Immunology 112(1): 8-23). Physiologically, the NKT-cells can augment or inhibit immune responses, including antitumor, autoimmune, and anti-pathogen responses, through a variety of mechanisms depending on context (Yue et al. (2010) The Journal of Immunology 184: 268-276), including induction of cell death in multiple myeloma cells. Conditions in which NKT-cells may be involved include autoimmune or inflammatory diseases, including myasthenia gravis, psoriasis, ulcerative colitis, primary biliary cirrhosis, colitis, autoimmune hepatitis, atherosclerosis, and asthma. In addition to cytokine release, NKT cell effector functions which result in cell lysis, such as perforin release and granzyme release and cell death, may also be relevant in conditions in which NKT cells are implicated, such as in cancer. Modulation of CD1d-mediated effects is therefore of potential therapeutic benefit.

There is an ongoing need for compounds that can bind and/or interact with CD1d as specific as possible, i.e. while minimally or not binding to other family members of the CD1-family, both in vitro and in vivo. In particular there is need for such compounds that bind and/or modulate (activate or inhibit) biological functions that involve CD1d such as, but not limited to, NKT-cell activation. Such compounds may, for example, show benefit in the various diseases in which CD1d-mediated functions play a role.

SUMMARY OF THE INVENTION

The present invention provides a compound comprising at least one single-domain antibody. The single-domain antibody binds to human CD1d. The single-domain antibody that binds to human CD1d comprises a CDR1, CDR3 and CDR3 region with an amino acid sequence as disclosed herein, and conservative sequence variants thereof.

Preferably the single-domain antibody has a CDR1, CDR2 and CDR3 region in the combination as disclosed herein, for example as shown in Tabel1.

Even more preferably, the single domain antibody has an amino acid sequence selected from the group of SEQ ID NO: 1-SEQ ID NO: 21.

The compound according to the invention may be any kind of compound, for example a complex, as long as the single-domain antibody that binds to human CD1d is comprised in the compound. Preferably the compound is a polypeptide. In certain embodiments the compound may consist of only the single-domain antibody that binds to human CD1d. In other embodiments the compounds consists of the single-domain antibody that binds to human CD1d and a label. In even further embodiments the compound may comprise the single-domain antibody that binds to human CD1d linked to a pharmaceutical active agent and/or other antibodies.

Also provided is use of the compound according to the invention in medical treatment and/or as a diagnostic agent.

Also provided is a pharmaceutical composition that comprises a compound as disclosed herein and nucleotide sequences and host cells comprising such nucleotide sequences that encode for the compounds according to the invention.

BRIEF DESCRIPTION OF THE DRAWINGS/FIGURES

FIG. 1: CD1d-specificity of individual selected nanobodies. Flow-cytometry was used to detect binding of isotype control mAb (IgG2b), anti-CD1d 51.1 mAb, R2 negative control VHH, and individual CD1d-specific VHH. Data demonstrate binding to CD1a, CD1b, CD1c, and CD1d transfected tumor cell lines (n=3).

Figure 2:
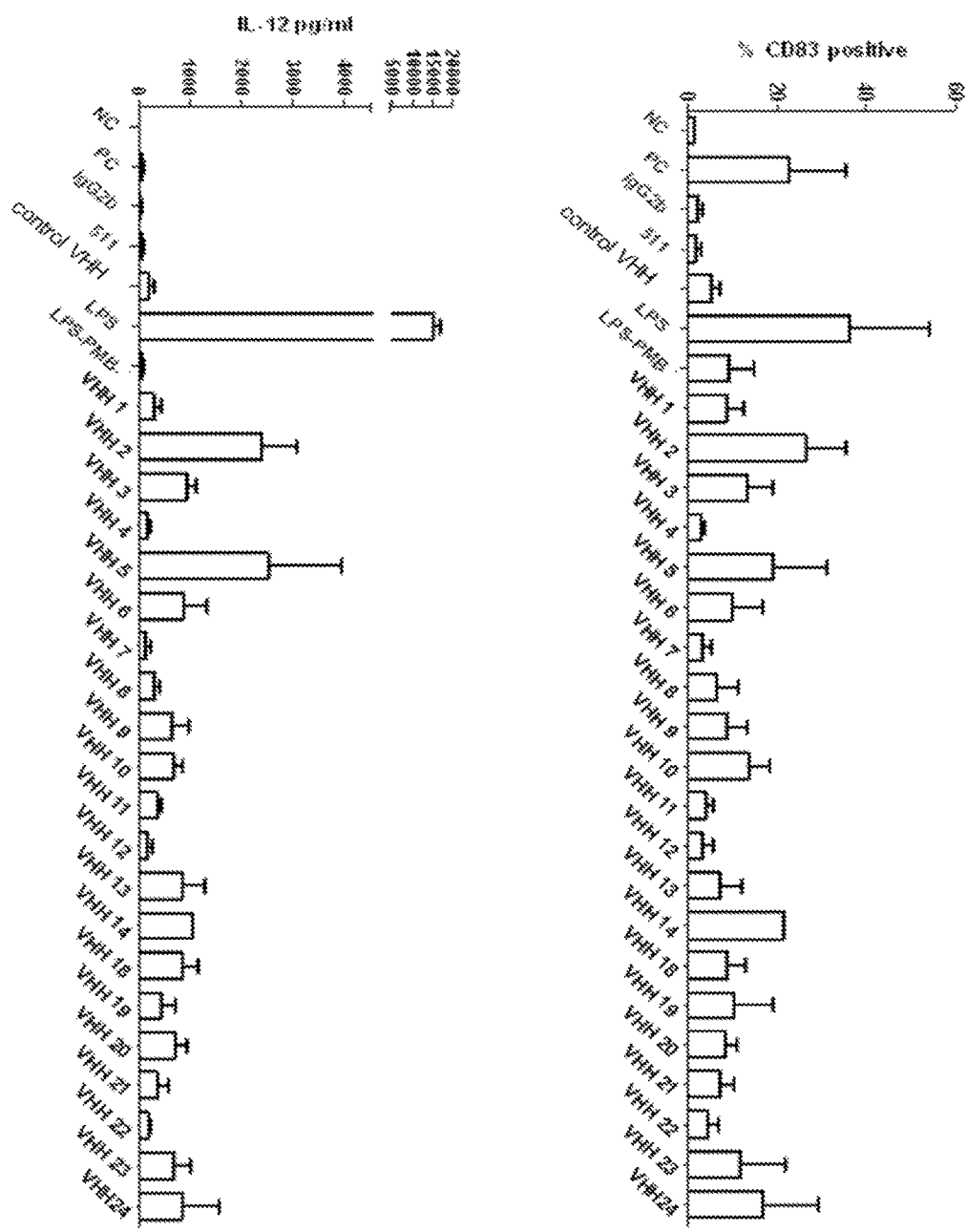

FIG. 2: Induction of moDC maturation and cytokine production by CD1d-specific nanobodies. Immature moDC were cultured with CD1d-specific nanobodies. After 24 hours, supernatants were harvested for detection of cytokine production (ELISA). After 72 h, moDC were analyzed for cell surface expression of the maturation marker CD83 using flow cytometry. NC=negative control, PC=positive control, IgG2b=isotype control mAb, 51.1=anti-CD1d 51.1 mAb, LPS=lipopolysaccharide, LPS-PMB=lipo-polysaccharide with polymyxin B. Data represent mean+SEM, n=3.

Figure 3:
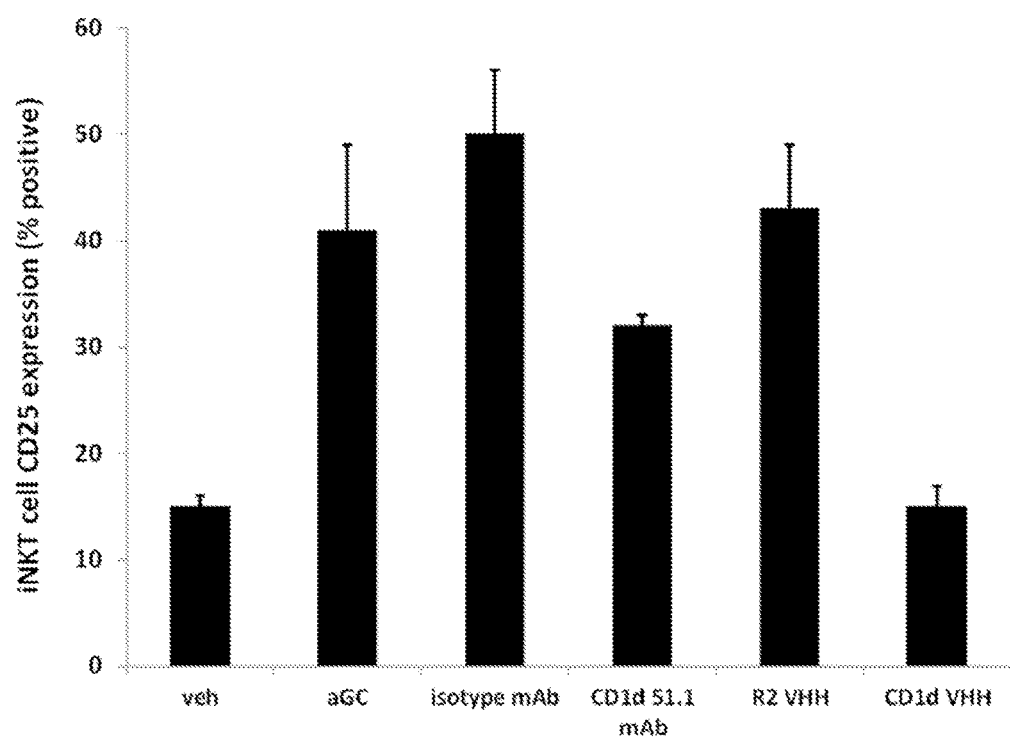

FIG. 3: Inhibition of α-GalCer induced iNKT cell activation. CD1d-transfected HeLa cells were pulsed overnight with vehicle control (veh) or α-GalCer (all other conditions). After washing, vehicle or α-GalCer pulsed HeLa-CD1d were cultured for 2 hours with IgG2b isotype control mAb, anti-CD1d 51.1 mAb, negative control VHH R2, or a neutralizing anti-CD1d VHH (VHH 24 (18-29c)) after which time iNKT cells were added. After 24 hr iNKT cell activation (CD25 expression) was determined using flow cytometry. Data indicate mean+SEM of 3 experiments. Superior neutralization of iNKT cell activation by anti-CD1d VHH.

Figure 4:
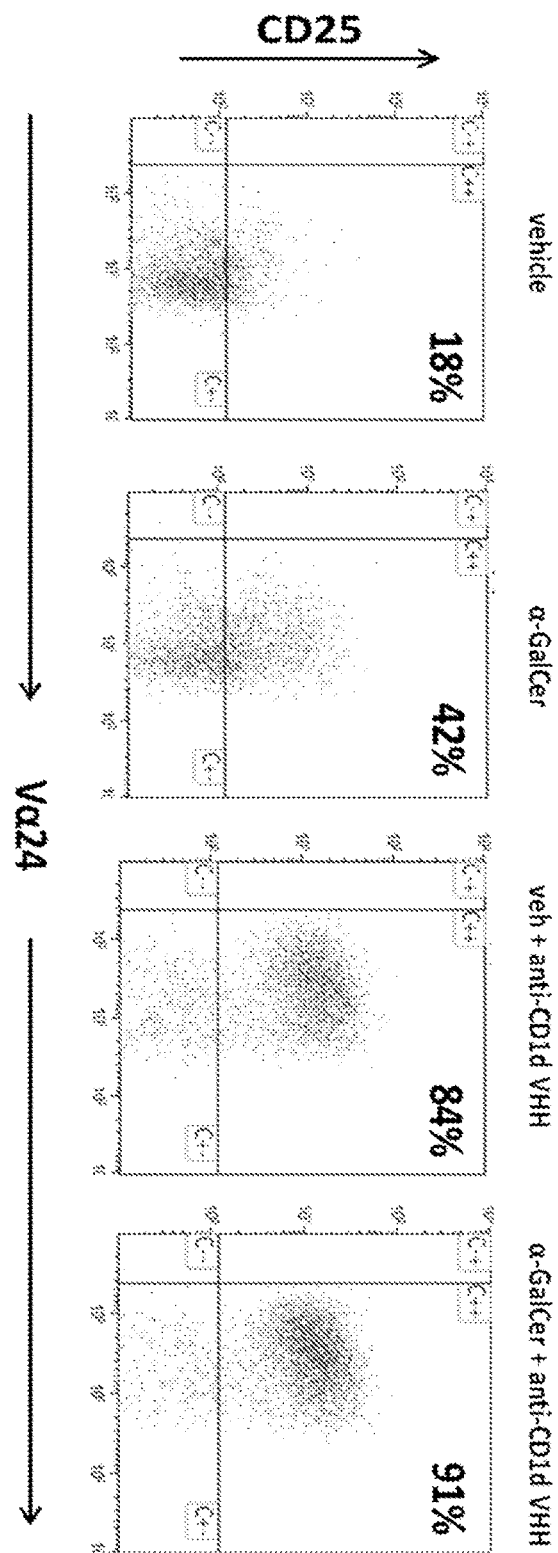

FIG. 4: Induction of iNKT cell activation. CD1d-transfected C1R cells were pulsed overnight with vehicle control (veh) or α-GalCer as indicated. After washing, vehicle or α-GalCer pulsed C1R-CD1d were cultured for 2 hours with or without a specific anti-CD1d VHH after which iNKT cells were added. After 24 hr iNKT cell activation (CD25 expression) was determined using flow cytometry. Representative flow cytometric dotplots demonstrating activation of iNKT cells by α-GalCer, but more strikingly after co-culture with the anti-CD1d VHH (VHH12 (18-14b)). Data are representative from multiple experiments with multiple CD1d-expressing tumor cell lines.

Figure 5:
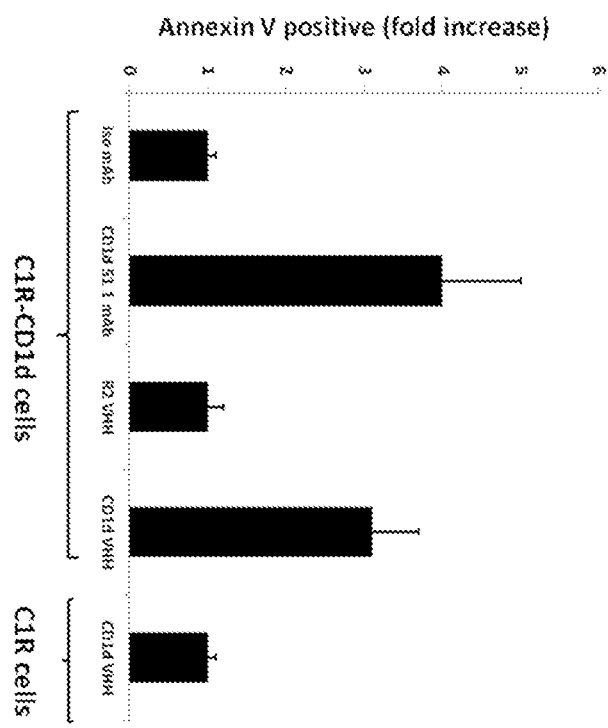

FIG. 5: Induction of annexin V binding by anti-CD1d nanobodies. C1R cells, CD1d-transfected C1R cells (left panel) and MM.1s cells and CD1d-transfected MM.1s cells (right panel) were cultured for 24 hours with IgG2b isotype control mAb, anti-CD1d 51.1 mAb, negative control VHH R2, or a CD1d-specific VHH (VHH19 (19-23G)). Percentage of target cells binding annexin V, which is suggestive of early apoptosis, was then determined by flow-cytometry. Data indicate mean+SEM of 3 experiments.

Figure 6:
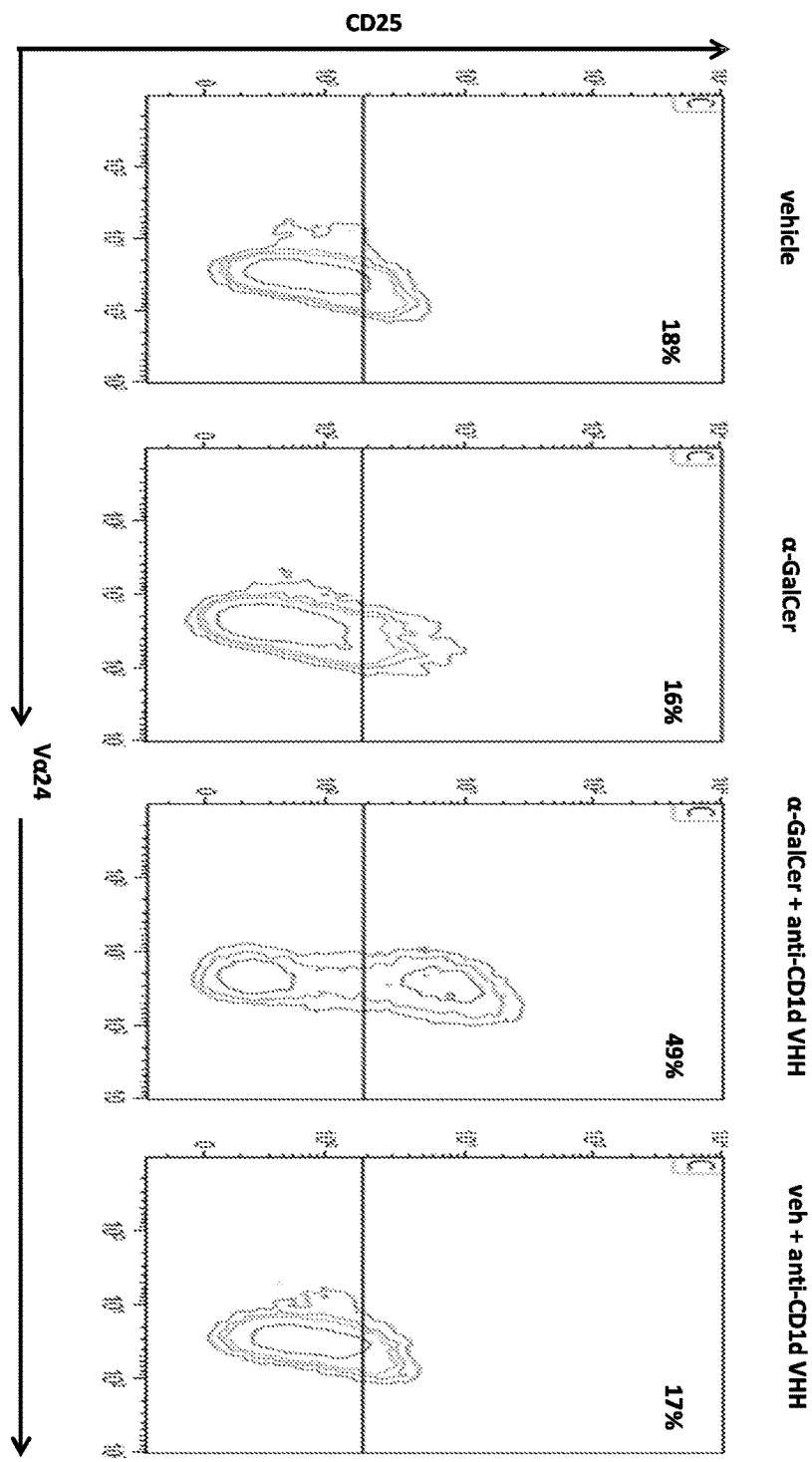

FIG. 6: Induction of iNKT cell activation using plate-bound β2m-human CD1d (±vehicle, α-GalCer and/or anti-CD1d VHH). 96-well plates were coated with a bispecific construct consisting of anti-EGFR VHH fused to β2m-hCD1d (loaded with either vehicle control or α-GalCer). Coated plates were cultured for 2 hours in the presence or absence of an anti-CD1d VHH (VHH12) after which iNKT cells were added. After 24 hours iNKT cell activation (CD25 expression) was determined using flowcytometry. Representative flowcytometric dotplots demonstrating slight activation of iNKT cells by α-GalCer-loaded β2m-hCD1d, but robust activation after co-culture of α-GalCer-loaded β2m-hCD1d with the anti-CD1d VHH (VHH12 (18-14b)).

Figure 7:
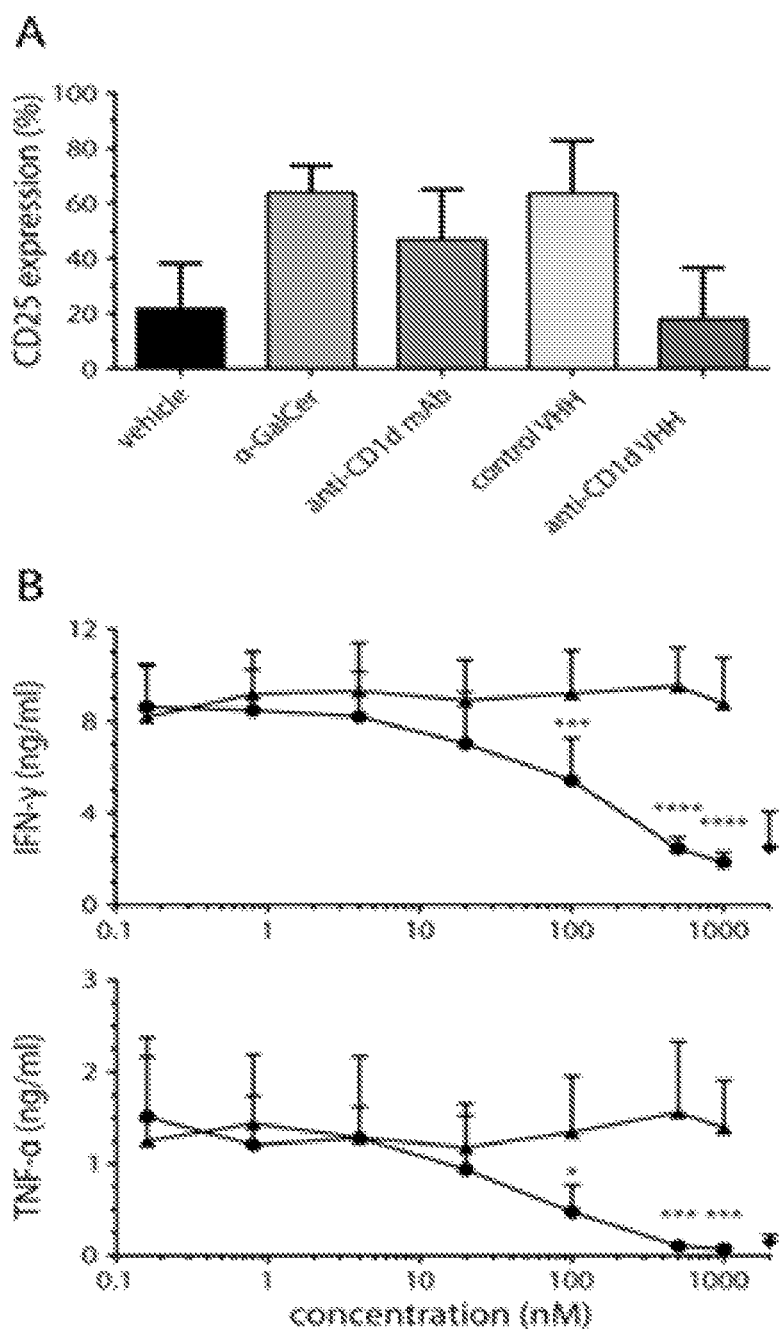

FIG. 7: Dose dependent inhibition of CD1d-α-GalCer mediated iNKT cell activation. iNKT CD25 expression, IFN-γ and TNF-α production were determined after a 24 h co-culture of iNKT with CD1d-transfected HeLa cells pulsed with vehicle control (vehicle) or α-GalCer (all other conditions) and medium (vehicle and α-GC), anti-CD1d mAb 51.1 (10 μg/ml), control VHH (500 nM) or anti-CD1d VHH (VHH24; 500 nM). Graphical representation showing CD25 expression on iNKT cells (a). Concentration dependent effect of anti-CD1d VHH (● symbols) and a control non-inhibitory but CD1d-specific VHH (▲ symbols) on IFN-γ and TNF-α production. ♦ indicate the vehicle loaded control condition (b). Mean+SD, n=3, p<0.05, p<0.01, ****p<0.0001. The tested VHH is VHH24.

Figure 8:
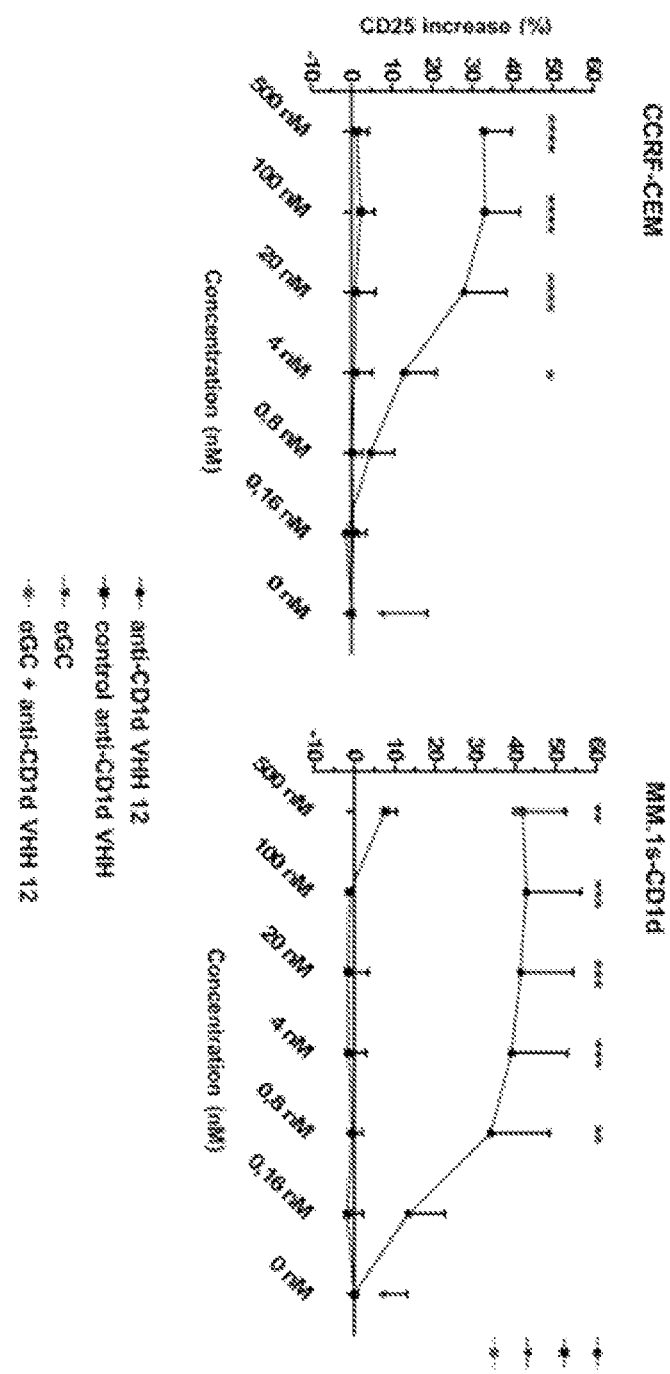

FIG. 8: Dose dependent iNKT cell activation by anti-CD1d VHH12. CCRF-CEM (T-ALL, CD1d positive; n=4) and CD1d-transfected MM.1s (multiple myeloma; n=3) cells were pulsed with vehicle control or αGC, incubated with anti-CD1d VHH and controls and co-cultured with iNKT for 24 h after which iNKT CD25 expression was determined. *p<0.05, p<0.01, *p<0.001, ****p<0.0001 (compare to FIG. 4).

Figure 9:
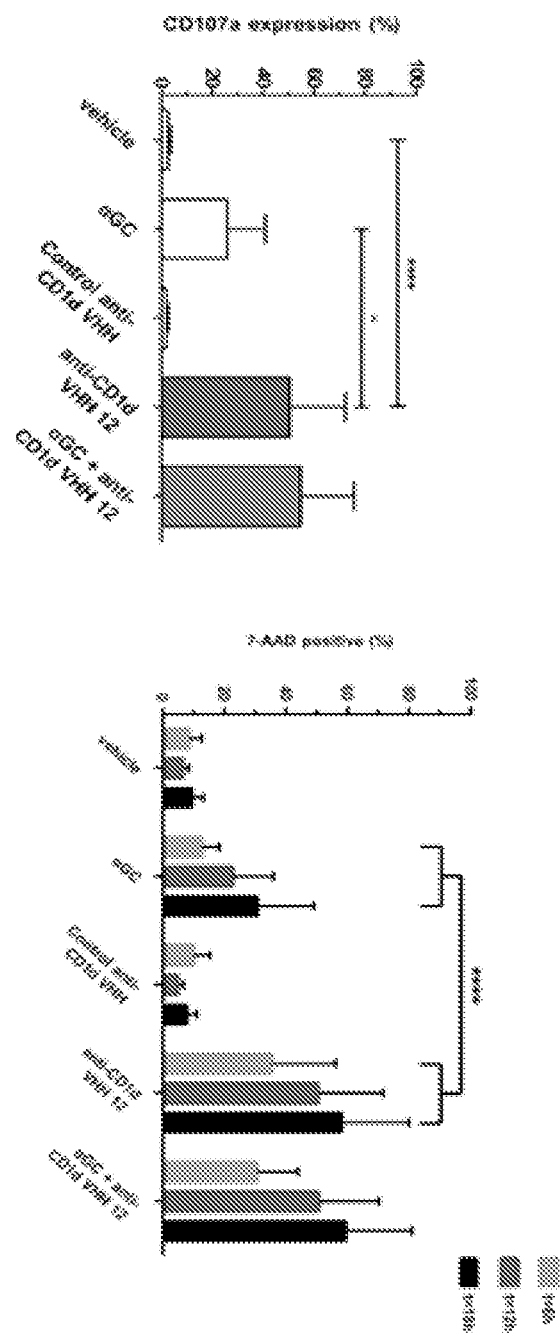

FIG. 9: Induction of iNKT cell degranulation (left) and cytotoxicity against CD1d+ tumor cells line (right). CCRF-CEM cells (CD1d-positive) were pulsed with vehicle control or αGC, incubated with anti-CD1d VHH and controls and co-cultured with iNKT (E:T ratio of 1:2) for the indicated time 6, 12 or 18 h) and stained with CD107a (t=4 h) or annexin V and 7-AAD for flow cytometry. N=5; *p<0.05; ***p<0.001. The anti-CD1d VHH shown is VHH12.

Figure 10:
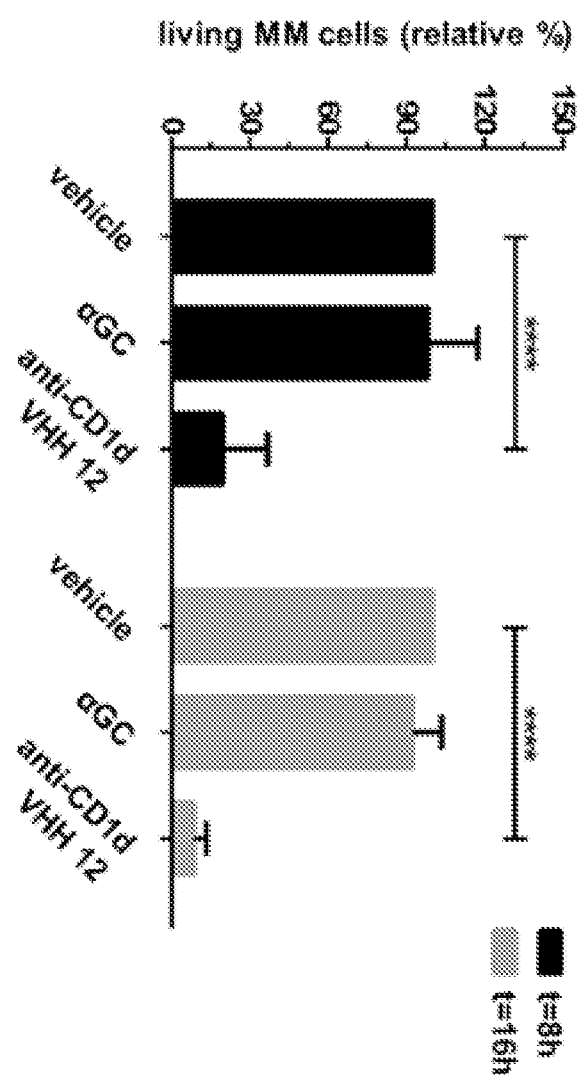

FIG. 10: Induction of iNKT cell cytotoxicity against CD1d+ primary multiple myeloma cells. Thawed primary bone marrow samples from MM patients were pulsed with vehicle control or αGC or incubated with anti-CD1d VHH and controls and then co-cultured with iNKT for the indicated time (8 and 16 h) after which the percentage of surviving MM cells was determined. The anti-CD1d VHH shown is VHH12.

Figure 11:
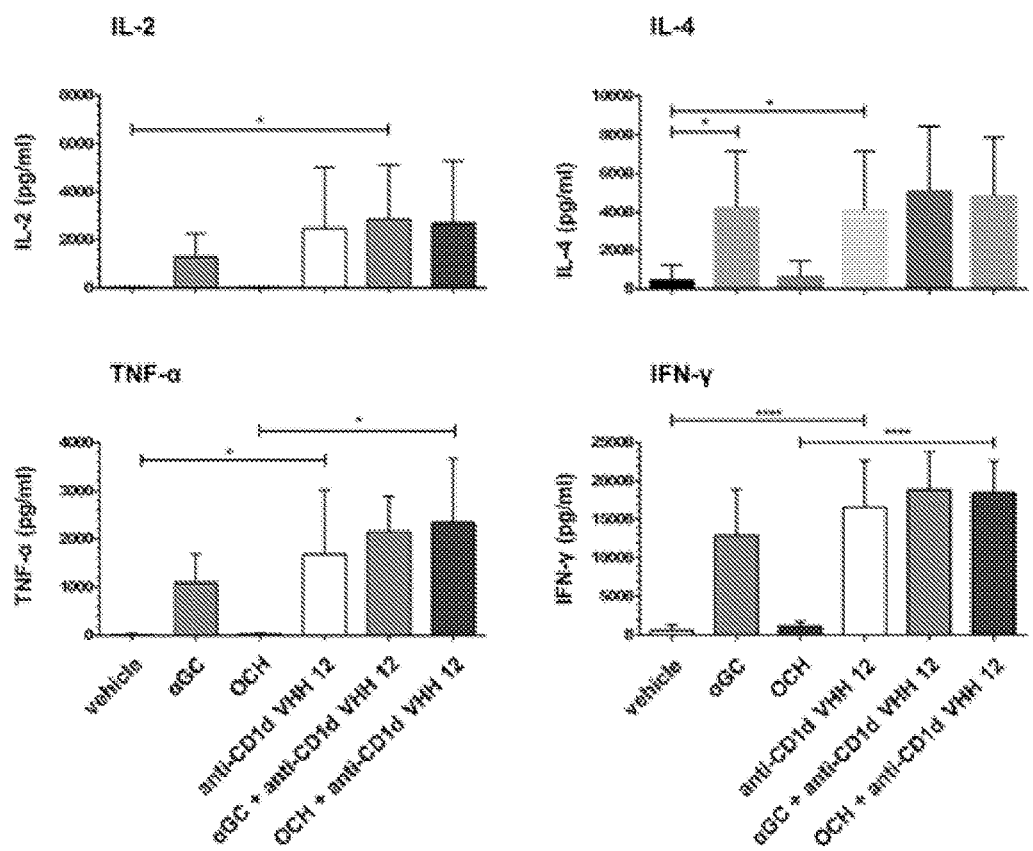

FIG. 11: Induction of iNKT cell cytokine production by anti-CD1d VHH12. For detection of cytokine production HeLa-CD1d cells were pulsed with vehicle control, OCH (a sphingosine truncated analog of alpha-galactosylceramide (alpha-GC); glycolipid reported to induce Th2-cytokine production in iNKT cells) or αGC, incubated with anti-CD1d VHH and controls and co-cultured with iNKT for 24 h after which supernatants were analyzed (by Cytometric Bead Assay; CBA). N=4; *p<0.05; ****p<0.0001.

DETAILED DESCRIPTION OF THE INVENTION

Definitions

In the following description and examples a number of terms are used. In order to provide a clear and consistent understanding of the specifications and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed in handbooks.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for using "a" compound, includes using a plurality of this compound (e.g. 10s, 100s, 1000s, 10s of thousands, 100s of thousands, millions, or more molecules).

With the term "aligning" and "alignment" is meant the comparison or amino acid sequences of two or more molecules/compounds based on the presence of short or long stretches of identical or similar amino acids. Several methods for alignment of amino acid sequences are known in the art, as will be further explained below.

"Sequence identity" is a measure of the identity of nucleotide sequences or amino acid sequences. In general, the sequences are aligned so that the highest order match is obtained. "Identity" per se has an art-recognized meaning and can be calculated using published techniques. Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity may be codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403). Sequence identity as disclosed herein was determined by calculating) the percentage of amino acids that are similar (number of amino acids similar to reference sequence divided by total number of amino acids in the reference sequence), essentially as outlined in the paragraph below.

As an illustration, by an amino acid sequence with at least, for example, 70% "sequence identity" to a reference amino acid sequence of SEQ ID NO: 1 it is intended that the amino acid sequence is identical to the reference sequence except that the polypeptide sequence may include up to 3 amino acid alterations per each of the 10 amino acids of the reference amino acid of SEQ ID NO: 1. Hence, the percentage of identity of an amino acid sequence to a reference amino acid sequence is to be calculated over the full length of the reference amino acid sequence. In other words, to obtain an amino acid sequence comprising at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

The terms "amino acid sequence" or "protein" or "peptide" refer to molecules consisting of a chain of amino acids, without reference to a specific mode of action, size, 3 dimensional structure or origin. A "fragment" or "portion" of thereof may thus still be referred to as an "amino acid sequence" or "protein" or "peptide". An "isolated amino acid sequence" is used to refer to an amino acid chain with a particular sequence and which is no longer in its original natural environment, for example in vitro or in a recombinant bacterial or human host cell.

Each immunoglobulin molecule has a variable domain. The variable domain of immunoglobulin molecules is subdivided into hypervariable (HV) and framework (FR) regions. HV regions have a high ratio of different amino acids in a given position, relative to the most common amino acid in that position. The hypervariability regions are referred to as complementarity determining regions (CDR). Immunoglobulin molecules have three complementarity determining regions (CDR1, CDR2 and CDR3). Four framework regions, with much less variable amino acids sequences, separate the CDR regions. The CDR regions can direct binding to the antigen, such as CD1d.

Description

The present invention generally relates to compounds comprising single-domain antibodies which bind to human CD1d. The present inventors have found single-domain antibodies and antigen-binding portions thereof which bind to human CD1d.

In a first aspect there is provided for a compound comprising at least one single-domain antibody which binds to human CD1d, wherein the single-domain antibody comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

As disclosed before, CD1d (Entrez Gene ID 912; NCBI Reference Sequence: NP_001757; Balk et al. (1989) Proc Natl Acad Sci USA 86:252-256) is expressed in a variety of cells including B-cells in chronic lymphocytic leukemia patients, hepatocytes, dendritic cells, and tumor cells and the single-domain antibodies disclosed herein can be used for binding to CD1d, for example, but not restricted to binding to CD1d on any of these cells or for binding to CD1d on other cells expressing CD1d, or for binding to CD1d molecules that are not bound to cells, and that are either not bound to anything, or are for example linked to or associated with carriers, polymers or other proteins.

The compound comprising the single-domain antibody which binds human CD1d can be any kind of compound or complex as long as it comprises a single-domain antibody which binds to CD1d. Preferably, the compound according to the invention can bind human CD1d due to the presence of the single-domain antibody which binds human CD1d.

The compound according to the invention may further comprise other function or non-functional groups. For example, the single-domain antibody of the current invention may be linked to a nanoparticle, a liposome, a virus, a label, another antibody or protein structure (e.g. a receptor) or may be fused to an antigen, peptide, a drug, a marker, or nucleic acid. For example, the compound may also comprise a magnetic bead, allowing the isolation of CD1d expressing cells.

The CD1d single-domain antibody may be linked via the carboxyl or amino terminus of the antibody, or may be linked at a site other than the carboxyl or amino termini. The attachment to the CD1d single-domain antibody may be direct, i.e., without any intermediate sequence, or through a linker amino acid sequence, a linker molecule, or a chemical bond. For example, the coupling may be of a physical and/or chemical type.

In one embodiment, the compound is a bi-specific antibody or a multi-specific antibody. In one embodiment, the compound is a bivalent antibody or a multivalent antibody. Bivalency or multi-valency can allow antibodies to bind to multimeric antigen with great avidity; bi-specificity or multi-specificity can allow the cross-linking of two antigens.

The compound comprises at least one single-domain antibody which binds to human CD1d, wherein the single-domain antibody comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

Single domain antibodies (sdAb, also called Nanobody by Ablynx, the developer, or VHH) are well known to the skilled person. Single domain antibodies are antibodies whose complementarity determining regions are part of a single domain polypeptide. Single domain antibodies thus comprise a single complementarity determining region (CDR) 1 (CDR1), a single CDR2 and a single CDR3. Examples of single domain antibodies are heavy chain only antibodies, antibodies that naturally do not comprise light chains, single domain antibodies derived from conventional antibodies, and engineered antibodies.

Single domain antibodies may be derived from any species including mouse, human, camel, llama, goat, rabbit, and bovine. For example, naturally occurring VHH molecules can be derived from antibodies raised in Camelidae species, for example in camel, dromedary, alpaca and guanaco.

Like a whole antibody, a single domain antibody is able to bind selectively to a specific antigen. Single domain antibodies may contain only the variable domain of an immunoglobulin chain having CDR1, CDR2 and CDR3 and framework regions. With a molecular weight of only about 12-15 kDa, nanobodies are much smaller than common antibodies (150-160 kDa) which are composed of two heavy chains and two light chains.

CDR1, CDR2 and CDR3 sequences may be exchanged between species. For example, from a llama immunoglobulin molecule, CDR sequences may be selected and exchanged with CDR sequences in a human immunoglobulin molecule, to obtain a human immunoglobulin molecule having the specificity that is derived from the llama CDR sequences. This may be advantageous as a human sequence may be less immunogenic to humans as compared to the original llama framework sequence. Such an exchange of CDR sequences is known as humanization.

Hence, the immunoglobulin molecules according to the invention may have human derived immunoglobulin sequences or llama derived immunoglobulin sequences and have the CDR1, CDR2 and CDR3 sequences replaced with the CDR sequences according to the invention in order to provide for human CD1d binding. In other words, the compound according to the invention may comprise a humanized single-domain antibody with CDRs as disclosed herein. For example, a single domain antibody may have human framework sequences and CDR regions as disclosed herein.

The single-domain antibody that is comprised in the compound according to the invention comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

The sequence of SEQ ID NO:22 correspond with the sequence of CDR1 of the single-domain antibody denoted as 17-1E in Table 1 herein. For the purpose of the current invention the single-domain antibody 17-1E may also be referred to as VHH number 1. The sequence of the single-domain antibody 17-1E is shown as SEQ ID NO:1 and comprises, in addition to the sequences of the CDR1, CDR2 and CDR3 as shown in Table 1 also the framework sequences.

The sequence with SEQ ID NO:43 correspond with the sequence of CDR2 of the single-domain antibody denoted as 17-1E in Table 1 herein.

For all single-domain antibodies described herein and, for example, as listed in Table 1, the region before CDR1 may be referred to as framework region (FW) 1, the region between CDR1 and CDR2 may be referred to as FW2, the region between CDR2 and CDR3 may be referred to as FW3, and the region after CDR3 may be referred to as FW4. The respective individual framework regions FW1, FW2, FW3 or FW4 can be easily established based on the sequences of the CDR1, CDR2 and CDR3 and the whole single-domain antibody, and are therefore disclosed as such.

It was surprisingly found that a variety of single-domain antibodies could be obtained that share a high amino acid sequence identity with respect to the CDR1 and CDR2 of the various single-domain antibodies. The CDR1, CDR2 and CDR3 sequences of the single-domain antibodies found are listed in Table 1. For example, the single-domain antibody denoted as 19-23G in Table 1 has VHH number 19, and has a combination of a CDR1 with a sequence that corresponds with SEQ ID NO:37, a CDR2 with a sequence that corresponds with SEQ ID NO: 58 and a CDR3 with a sequence that corresponds with SEQ ID NO: 79. The whole sequence, including framework regions of this VHH is SEQ ID NO: 16.

However, according to the invention the single-domain antibody may comprise any combination of a CDR1, CDR2 and CDR3 as long as CDR1 shows at least 60% sequence identity with SEQ ID NO: 22 and CDR2 comprises an amino acid sequence that has at least 60% sequence identity with SEQ ID NO: 43. For example, also contemplated is that the single-domain antibody comprises a CDR1 as shown in Table 1 of a first VHH (for example VHH nr 10) and a CDR2 as shown in Table 1 of a second VHH (for example VHH nr 20).

In other words, it will be appreciated that, based on the present disclosure, the skilled person can, without undue burden, provide compounds according to the invention, comprising at least one single-domain antibody which binds to human CD1d, wherein the CDR1 of the single-domain antibody comprises an amino acid sequence that has at least 60% sequence identity with SEQ ID NO: 22 and the CDR2 of the single-domain antibody comprises an amino acid sequence that has at least 60% sequence identity with SEQ ID NO: 43. For example, based on the various CDR1s and CDR2 shown in Table 1.

In a preferred embodiment CDR1 over its entire length shows at least 60% sequence identity with SEQ ID NO: 22. In a preferred embodiment CDR2 over its entire length shows at least 60% sequence identity with SEQ ID NO: 43. Preferable, CDR1 over its entire length shows at least 60% sequence identity with SEQ ID NO: 22 and CDR2 over its entire length shows at least 60% sequence identity with SEQ ID NO: 43. Preferably CDR1 and/or CDR2 shows at least 65%, 70%, 75%, 80%, 90%, 95%, 97%, 99% identity with respectively SEQ ID NO:22 and/or SEQ ID NO: 43.

Also provided is a compound comprising at least one single-domain antibody which binds to human CD1d, wherein the single-domain antibody comprises complementarity determining regions CDR1, CDR2 and CDR3 and wherein CDR1 comprises an amino acid sequence that has at least 90% sequence identity with SEQ ID NO: 22, CDR2 comprises an amino acid sequence that has at least 80% sequence identity with SEQ ID NO: 43, and CDR3 comprises an amino acid sequence that has at least 70% sequence identity with SEQ ID NO: 64; or wherein CDR1 comprises an amino acid sequence selected from the group consisting of SEQ ID NO: 33 and SEQ ID NO: 42, CDR2 comprises an amino acid sequence selected from the group consisting of SEQ ID NO: 54 and SEQ ID NO: 63 and CDR3 comprises an amino acid sequence selected from the group consisting of SEQ ID NO: 75 and SEQ ID NO: 84.

It was found that within the provided single-domain antibodies that can be comprised in the compound according to the present invention, a group is present that displays for the CDR1 an amino acid sequence that has at least 90% sequence identity with SEQ ID NO: 22, for the CDR2 an amino acid sequence that has at least 80% sequence identity with SEQ ID NO: 43 and for the CDR3 an amino acid sequence that has at least 70% sequence identity with SEQ ID NO: 64. These single-domain antibodies share a high degree of identity with respect to the respective complementarity determining regions. In a preferred embodiment CDR1 over its entire length shows at least 90% sequence identity with SEQ ID NO: 22. In a preferred embodiment CDR2 over its entire length shows at least 80% sequence identity with SEQ ID NO: 43. In a preferred embodiment CDR3 over its entire length shows at least 70% sequence identity with SEQ ID NO: 64. Preferable, CDR1 over its entire length shows at least 90% sequence identity with SEQ ID NO: 22, CDR2 over its entire length shows at least 80% sequence identity with SEQ ID NO: 43 and CDR3 over its entire length shows at least 70% sequence identity with SEQ ID NO: 64. Preferably CDR1 shows at least 90%, 92%, 95%, 97%, 99% identity with SEQ ID NO:22, CDR2 shows at least 80%, 82%, 85%, 90%, 92%, 95%, 97%, 99% identity with SEQ ID NO: 43 and CDR3 shows at least 70%, 72%, 75%, 78%, 80%, 82%, 85%, 90%, 92%, 95%, 97%, 99% identify with SEQ ID NO: 64.

According to the invention, in a preferred embodiment, the single-domain antibody may comprise any combination of a CDR1, CDR2 and CDR3 as long as CDR1 shows at least 90% sequence identity with SEQ ID NO: 22 and CDR2 comprises an amino acid sequence that has at least 80% sequence identity with SEQ ID NO: 43 and CDR3 comprises an amino acid sequence that has at least 70% identity with SEQ ID NO:64. For example, also contemplated is that the single-domain antibody comprises a CDR1 as shown in Table 1 of a first VHH (for example VHH nr 10; SEQ ID NO: 31) and a CDR2 as shown in Table 1 of a second VHH (for example VHH nr 20; SEQ ID NO: 59), and a CDR3 as shown in Table 1 of the first or second VHH or of a third VHH (for example VHH nr 21; SEQ ID NO: 81).

In other words, it will be appreciated that, based on the present disclosure, in a preferred embodiment, the skilled person can, without undue burden, provide compounds according to the invention, comprising at least one single-domain antibody which bind to human CD1d by combining different CDR1, CDR2 and CDR3's, wherein the CDR1 of the single-domain antibody comprises an amino acid sequence that has at least 90% sequence identity with SEQ ID NO: 22 and the CDR2 of the single-domain antibody comprises an amino acid sequence that has at least 80% sequence identity with SEQ ID NO: 43 and the CDR3 of the single-domain antibody comprises an amino acid sequence that has at least 70% sequence identity with SEQ ID NO: 64. For example, based on the various CDR1, CDR2 and CDR3 shown in Table 1.

In another preferred embodiment, there is provided a compound comprising at least one single-domain antibody which binds to human CD1d, wherein the single-domain antibody comprises complementarity determining regions CDR1, CDR2 and CDR3 wherein CDR1 comprises an amino acid sequence selected from the group consisting of SEQ ID NO: 33 and SEQ ID NO: 42, CDR2 comprises an amino acid sequence selected from the group consisting of SEQ ID NO: 54 and SEQ ID NO: 63 and CDR3 comprises an amino acid sequence selected from the group consisting of SEQ ID NO: 75 and SEQ ID NO: 84.

Preferably, there is provided for compound comprising at least one single-domain antibody which binds to human CD1d as disclosed herein, wherein the single-domain antibody has complementarity determining regions CDR1, CDR2 and CDR3 as listed in combination in Table 1, or conservative sequence variants thereof.

Although it will be appreciated that the skilled person will be able to provide for various single-domain antibodies based on the various CDR1, CDR2, CDR3 as disclosed herein, as well as the other sequences provided (including the various framework sequences and the full-length sequence of the single-domain antibodies), preferably the single-domain antibody has a CDR1, CDR2 and a CDR3 as shown in combination in Table 1, and conservative sequence variants thereof. In other words, a compound according to the invention comprises a single-domain antibody wherein, preferably, the CDR1 and the CDR2 and the CDR3 are of one and the same VHH as shown in Table 1. For example, the single-domain antibody has the CDR1, CDR2 and CDR3 of the same VHH as shown in Table 1, for example of VHH1, VHH2, VHH3 . . . VHH14, VHH18, VHH 19 . . . VHH24. It was found that in particular CDR1, CDR2 and CDR3 as shown in combination (i.e. from the same VHH) show beneficial CD1d binding. As will be appreciated by the skilled person, also included are conservative sequence variants of the CDR1, CDR2 and CDR3 combinations as disclosed in Table 1.

Indeed in determining the degree of sequence identity between two amino acid sequences or in establishing the CDR1, CDR2 and CDR3 combination in the single-domain antibody, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, WO 00/46383, WO 01/09300 and WO 04/037999. Conservative substitutions preferably are substitutions in which one amino acid within the following groups (a)-(e): An amino acid residue is substituted by another amino acid residue within the same group (a)-(e): (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Preferred examples of conservative substitutions are as follows: Ala into Gly or into Ser; Arg into Lys; Asn into Gln or into His; Asp into Glu; Cys into Ser, Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr, Ser into Thr; Thr into Ser, Trp into Tyr; Tyr into Trp; and/or Phe into Val, into Ile or into Leu.

Preferably, the single-domain antibody has complementarity determining regions CDR1, CDR2 and CDR3 as listed in combination in Table 1, including conservative sequence variants thereof. More preferably, the single-domain antibody has complementarity determining regions CDR1, CDR2 and CDR3 as listed in combination in Table 1.

Also provided is a compound as disclosed herein and above wherein the compound comprises an amino acid sequence selected from the group consisting of SEQ ID NO: 1-SEQ ID NO: 21, or conservative sequence variants thereof.

In other words, preferably, the single-domain antibody comprised in the compound according to the invention comprises or consists of an amino acid sequence selected from the group consisting of SEQ ID NO: 1-SEQ ID NO: 21, or, as explained above, conservative sequence variants thereof. These sequences 1-22 represent single-domain antibodies with the CDR1, CDR2 and CDR3 as shown in combination in Table 1, including the framework regions. These single-domain antibodies and there CD1d binding properties as described in detail in the Examples disclosed herein. SEQ ID NO:1 corresponds with VHH nr 1; SEQ ID NO:2 corresponds with VHH nr 2; SEQ ID NO: 3 corresponds with VHH nr 3; SEQ ID NO:4 corresponds with VHH nr 4; SEQ ID NO:5 corresponds with VHH nr 5; SEQ ID NO: 6 corresponds with VHH nr 6; SEQ ID NO:7 corresponds with VHH nr 7; SEQ ID NO:8 corresponds with VHH nr 8; SEQ ID NO: 9 corresponds with VHH nr 9; SEQ ID NO:10 corresponds with VHH nr 10; SEQ ID NO:11 corresponds with VHH nr 11; SEQ ID NO: 12 corresponds with VHH nr 12; SEQ ID NO:13 corresponds with VHH nr 13; SEQ ID NO:14 corresponds with VHH nr 14; SEQ ID NO: 15 corresponds with VHH nr 18; SEQ ID NO:16 corresponds with VHH nr 19; SEQ ID NO: 17 corresponds with VHH nr 20; SEQ ID NO:18 corresponds with VHH nr 21; SEQ ID NO:19 corresponds with VHH nr 22; SEQ ID NO: 20 corresponds with VHH nr 23; and SEQ ID NO:21 corresponds with VHH nr 24 as shown in Table 1.

Also provided are single-domain antibodies comprised in the compound according to the invention and that has at least 70%, 80%, 85%, 90%, 92%, 95%, 96%, 97%, 98% or at least 99% amino acid sequence identity with a sequence selected from the group consisting of SEQ ID N: 1-21, over its entire length (and as applicable for all sequence disclosed herein).

Although the compound according to the invention may be any kind of compound comprising a single-domain antibody that binds CD1d, in a preferred embodiment the compound is a polypeptide to which a pharmaceutical active agent or a label or a marker is attached. For example, the polypeptide, comprising the CD1d binding single-domain antibody may be linked to a pharmaceutical active agent that preferably is delivered to a CD1d expressing cell. Another example includes a compound according to the invention that comprises a CD1d-binding single-domain antibody and an antigen. Such compounds may find use in, for example, dendritic cell-based vaccines. The active agent may be linked to the compound according to the invention, preferably the polypeptide according to the invention, allowing release of the agent on its site of delivery. Another example is wherein the compound according to the invention, for example, the polypeptide according to the invention comprises a label. The label may be in the form of, for example, a fluorescent or radioactive label, but is not limited thereto.

Any kind of label that allows for detecting the presence of or the localization of the compound according to the invention can suitably be used within the context of the invention. In another embodiment, the compound is a polypeptide.

However, and in addition, in another preferred embodiment of the invention, there is provided for a compound according to any of the previous claims wherein the compound comprises further single domain antibodies, wherein the compound comprises a label, wherein a pharmaceutical active agent is linked to the compound, wherein the single-domain antibody is humanized, wherein the compound is a bispecific or multispecific compound (bi-specificity or multi-specificity can allow the cross-linking of two antigens), wherein the compound is a bivalent or multivalent compound (bivalency or multi-valency can allow antibodies to bind to multimeric antigen with great avidity), wherein the compound is fused to an antigen, a peptide or a nucleotide sequence, wherein the compound is a liposome, a virus, and/or wherein the compound is a nanoparticle.

Also provided is a compound as disclosed herein wherein the single domain antibody binds to human CD1d but not to human CD1a, human CD1b and/or human CD1c. In other words, within the particular use intended, the compound according to the invention comprises a single domain antibody which specifically binds to human CD1d and not human CD1a, CD1b and/or CD1c. Preferable the compound according to the invention does bind to human CD1d and not to human CD1a, CD1b and/or CD1c. The single domain antibodies represented by SEQ ID NO 1-21 are examples of single domain antibodies that specifically bind with human CD1d. The skilled person knows how to determine without undue burden whether a single domain antibody is specific for human CD1d, as can be witnessed from the Examples.

As mentioned herein, it was surprisingly found that there can be provided for compounds comprising CD1d binding single domain antibodies that share high amino acid identity amongst them with respect to the CDR1, CDR2 and/or CDR3 sequences. In addition, it was found that there can be provided for compounds, comprising the single-domain antibodies as described herein, with different functional characteristics and features, as can be witnessed from the Examples. Therefore, there is also provided for a compound as taught herein, wherein the compound is capable of inducing maturation of dendritic cells, preferably of monocyte derived dendritic cells, preferably wherein the single-domain antibody has the complementarity determining regions CDR1, CDR2 and CDR3 as listed in combination for VHH2 or VHH5 in Table 1, or conservative sequence variants thereof, or wherein the single-domain antibody is VHH2 or VHH5 or conservative sequence variants thereof; and/or the compound is capable of inhibiting glycolipid, for example alpha-galactosyl ceramide, induced CD1d-restricted T-cell, such as invariant natural killer T-cell, activation, preferably wherein the single-domain antibody has the complementarity determining regions CDR1, CDR2 and CDR3 as listed in combination for VHH5 or VHH24 in Table 1, or conservative sequence variants thereof or wherein the single-domain antibody is VHH5 or VHH24 or conservative sequence variants thereof; and/or the compound is capable of inducing activation of CD1d-restricted T cells, such as invariant natural killer T-cells and/or stimulating glycolipid (e.g. alpha-galactosyl ceramide) induced activation of CD1d-restricted T cells, such as invariant natural killer T-cell, preferably wherein the single-domain antibody has the complementarity determining regions CDR1, CDR2 and CDR3 as listed in combination for VHH12 in Table 1, or conservative sequence variants thereof or wherein the single-domain antibody is VHH12 or conservative sequence variants thereof; and/or the compound is capable of inducing annexin V binding (for example, binding of annexin V to cells that were contacted with such compound; annexin V binding is a marker of early apoptosis) and/or apoptosis in CD1d-expressing cells, preferably CD1d-expressing tumor, preferably wherein the single-domain antibody has the complementarity determining regions CDR1, CDR2 and CDR3 as listed in combination for VHH3, VHH6, VHH5, or VHH19 in Table 1, or conservative sequence variants thereof, or wherein the single-domain antibody is VHH3 or VHH6 or VHH8 or VHH19 or conservative sequence variants thereof.

It was found that the single-domain antibodies VHH2 and VHH5, with the CDR's as shown in Table 1, show activity towards inducing maturation of dendritic cells, preferably of monocyte derived dendritic cells (see Examples), as well as cytokine production, exemplified by IL-12. Compounds comprising such single domain antibodies are useful in inducing dendritic cell maturation and cytokine production, e.g. IL-12 production, in vitro or in vivo, for example in the treatment of cancers, malaria and HIV and/or as an antimicrobial or anti-viral agent. In addition, CD1d-triggering on dendritic cells can be useful in vaccination approaches, as discussed herein (see, for example, Yue et al. (2010) J Immunol. 184(1):268-76; Yue et al. (2005) Proc Natl Acad Sci USA. 102(33):11811-6; Teng et al. (2009) J Immunol. 182(6):3366-71; or Teng et al. (2009) J Immunol. 183(3):1911-20)

In addition, it was found (see Examples) that there can be provided for a compound according to the invention that is capable of inhibiting glycolipid, i.e. all glycolipids that can be bound/presented by CD1d, for example, alpha-galactosyl ceramide, induced CD1d-restricted T-cell, such as invariant natural killer T-cell, activation, preferably wherein the single-domain antibody has the complementarity determining regions CDR1, CDR2 and CDR3 as listed for VHH5 or VHH24 in combination in Table 1, or conservative sequence variants thereof. Compounds comprising such single domain antibodies are useful in inhibiting glycolipid (e.g. alpha-galactosyl ceramide) induced CD1d-restricted T cell (including invariant natural killer T-cell) activation both in vitro or in vivo, for example in research and/or for rescueing iNKT (invariant Natural Killer T-cells) cells or other CD1d restricted T cell subsets from chronic overstimulation (see, for example, Terabe et al. (2014) Cancer Immunol Immunother. 63(3):199-213).

Furthermore there is provided for a compound according to the invention that is capable of inducing activation of CD1d-restricted T cells, including invariant natural killer T-cells and/or stimulating glycolipid (e.g. alpha-galactosyl ceramide) induced activation of CD1d-restricted T cells, including invariant natural killer T-cells, preferably wherein the single-domain antibody has the complementarity determining regions CDR1, CDR2 and CDR3 as listed in combination for VHH12 in Table 1, or conservative sequence variants thereof. Compounds comprising such single domain antibodies are useful in inducing invariant natural killer T-cell activation in the absence of exogenously added glycolipids and/or stimulating glycolipid (including alpha-galactosyl ceramide) induced invariant natural killer T-cell activation both in vitro or in vivo, for example in the treatment of cancer. iNKT cells can exert tumor cytotoxicity via (1) direct lysis of tumor cells or via (2) production of immunoregulatory cytokines (e.g. after interacting with DC) such as IFN-γ that trigger secondary immune effectors such as NK cells, cytotoxic T cells to exert the antitumor effect. This is reviewed e.g. in Schneiders et al. (2011) Clin Immunol. 140(2):130-41.

In addition there is provided for a compound according to the invention that can bind to a CD1d targeting construct allowing targeting and targeted activation of iNKT cells at a tumor site, preferably wherein the single-domain antibody has the complementarity determining regions CDR1, CDR2 and CDR3 as listed in combination for VHH12 in Table 1, or conservative sequence variants thereof, preferably wherein the single-domain antibody is VHH12. This is useful and builds upon an approach put forward by Stirnemann K et al. J Clin Invest. 2008 March; 118(3):994-1005.

Also provided is a compound that is capable of inducing an increase in annexin V binding, which is suggestive of early apoptosis, and/or inducing apoptosis in CD1d-expressing cells, preferably CD1d-expressing tumor, preferably wherein the single-domain antibody has the complementarity determining regions CDR1, CDR2 and CDR3 as listed in combination for VHH3, VHH6, VHH8, or VHH19 in Table 1, or conservative sequence variants thereof. Compounds comprising such single domain antibodies are useful in inducing an increase in annexin V binding and/or apoptosis in CD1d-expressing cells both in vitro or in vivo, for example in the treatment of cancer. This is of use in, for example, CD1d+ malignancies where it can lead to cell death, for example in multiple myeloma (Blood. 2009 Mar. 12; 113(11):2498-507).

Also provided is for the use of such compounds comprising single domain antibodies with the different functionalities as described above, for example in the treatment of a condition in which such functionality is beneficial.

In a further preferred embodiment there is provided for a compound as described herein wherein the compound is a single domain antibody, preferably wherein the compound is a single domain antibody that has complementarity determining regions CDR1, CDR2 and CDR3 as listed in combination in Table 1, or conservative sequence variants thereof, or wherein the single domain antibody has an amino acid sequence selected from the group consisting of SEQ ID NO: 1-SEQ ID NO: 21, or conservative sequence variants thereof.

Also provided is a compound comprising an antibody, preferably a single-domain antibody which binds to human CD1d, wherein the antibody, preferably single-domain antibody comprises complementarity determining regions CDR1, CDR2 and CDR3 wherein CDR1, CDR2 and CDR 3 has an amino acid sequence that has at least 80%, 90%, 95% or 100% amino acid sequence identity to the amino acid sequence of respectively CDR1, CDR2 and CDR3 as shows for VHH nr 1, 2, 3, 4, 5, 6, 7, 8, 9, 10, 11, 12, 13, 14, 18, 19, 20, 21, 22, 23 or 24 as shown in Table 1. Preferably the compound, comprising an antibody, preferably a single-domain antibody has an amino acid sequence that has at least 80%, 90%, 95% or 100% amino acid sequence identity to the amino acid sequence of VHH nr 1, 2, 3, 4, 5, 6, 7, 8, 9, 10, 11, 12, 13, 14, 18, 19, 20, 21, 22, 23 or 24 as shown in Table 1, or conservative sequence variants thereof. Preferably to compound is an antibody, preferably a single stranded antibody. Each of the specific antibodies shown in table 1, or antibodies comprises the CDR1, CDR2, CDR3 as shown in combination therein (i.e. per VHH number) have surprising and non-obvious properties as shown in the examples and description. Also provided is a nucleic acid, or vector comprising such nucleic acid encoding for a CDR1, CDR2, and/or CDR3, antibody, single-domain antibody or compound according to the invention, as disclosed herein.

As will be appreciated by the skilled person, the compounds as described herein may have a wide variety of uses, including as a research tool, as a diagnostic tool, as means for delivery to a target site (expressing CD1d) of, for example, a drug, both in vitro and in vivo, in targeting two or more different receptors, molecules and/or antigens (e.g. wherein the compound is bi-specific or multi-specific), both in vitro and in vivo, and so on. Preferably the compound as described herein is for use in medical treatment, or for in vivo use as a diagnostic agent. Conditions that may benefit from the compound disclosed herein include, but are not limited to, cancer, HIV, malaria, asthma, allergy, autoimmune diseases, inflammatory bowel diseases and graft-versus-host-disease (GVHD). Therefore, in another embodiment, there is provided for a pharmaceutical composition comprising a compound according to the invention, for example comprising a single-domain antibody as described herein. As will be understood by the skilled person, the pharmaceutical composition may comprise another compound in addition to the compounds as disclosed herein, for example other pharmaceutical active ingredients and/or excipients.

Also provided is for the use of a compound as described herein, wherein the compound is used in vitro or wherein the compound is used in an in vitro diagnostic method, for example to detect CD1d expression in samples obtained from a patient, and/or to detect cells expressing CD1d.

According to another aspect of the invention, there is provided for a nucleotide sequence that encodes a compound as described herein. In this embodiment, the compound according to the invention is a polypeptide, for example the compound is a single domain antibody, for example with a sequence selected from the group consisting of SEQ ID NO: 1-21, and conservative sequence variants thereof.

The sequences as disclosed herein relate to amino acid sequences. Hence, the skilled person is well capable of providing for a nucleotide sequence encoding an amino acid sequence, as it only requires using a codon table to convert amino acid sequence into nucleotide sequence.

Such nucleotide sequence may be used to operably link it to promoter sequences, polyA signals etc., to provide for a genetic construct with which the antibody may be expressed. Such a genetic construct comprising the nucleotide sequence may be comprised in a host cell. Such host cell or non-human organism comprising a nucleotide sequence according to the invention is also provided for.

In a preferred embodiment there is provided for a nucleotide sequence as disclosed herein, and that encodes for a compound comprising an amino acid sequence selected from the group consisting of SEQ ID NO: 22-SEQ ID NO: 42, or conservative sequence variants thereof and/or an amino acid sequence selected from the group consisting of SEQ ID NO: 43-SEQ ID NO: 63, or conservative sequence variants thereof and/or an amino acid sequence selected from the group consisting of SEQ ID NO: 64-SEQ ID NO: 84, or conservative sequence variants thereof.

Also provided is for a method for preparing a compound as disclosed herein, wherein the method comprises allowing a host cell comprising a nucleic acid according to the invention to express the compound; and obtaining the compound. Methods for expression and obtaining are readily known to the skilled person.

Finally, also provided is an antibody that comprises a CDR1 and/or CDR2 and/or CDR3, preferably a CDR1 and CDR2, even more preferably a CDR1, CDR2 and CDR3, wherein the CDR1 has an amino acid sequence selected from the group consisting of SEQ ID NO: 22-SEQ ID NO: 42, or conservative sequence variants thereof, the CDR2 has an amino acid sequence selected from the group consisting of SEQ ID NO: 43-SEQ ID NO: 63, or conservative sequence variants thereof and CDR3 has an amino acid sequence selected from the group consisting of SEQ ID NO: 64-SEQ ID NO: 84, or conservative sequence variants thereof. Preferably the complementarity determining regions CDR1, CDR2 and CDR 3 have an amino acid sequence that has at least 80%, 90%, 95% or 100% amino acid sequence identity to the amino acid sequence of respectively CDR1, CDR2 and CDR3 as shows for VHH nr 1, 2, 3, 4, 5, 6, 7, 8, 9, 10, 11, 12, 13, 14, 18, 19, 20, 21, 22, 23 or 24 as shown in Table 1.

The antibody may be any type of antibody, including a single domain antibody, a single chain antibody, a humanized antibody, a 4-chain antibody or any other immunoglobulin molecule. The antibody may be linked to other function or non-functional groups, for example the antibody may be a bi-specific or multi-specific antibody, and/or a bi-valent or multi-valent antibody, may comprise a label of be fused to e.g. a nanoparticle, a drug, a peptide, a nucleic acid, and so on, and as disclosed herein above. The antibody may be used in treatment of a (human) patient for example, in the treatment of cancer, or may be used to bind and detect human CD1d and/or cells expressing human CD1d.

Where the provided SEQ ID NO 22-84 in the sequence listing differs from the sequences shown in Table 1, the sequence shown in Table 1 prevails.

TABLE 1

VHH number, VHH reference number as used herein, and sequence of CDR1, CDR2 and CDR3 of the various CD1d antibodies of the invention.

| VHH nr (SEQ ID) | VHH ref | CDR1 (SEQ ID 22-42) | CDR2 (SEQ ID 43-63) | CDR3 (SEQ ID 64-84) |
|---|---|---|---|---|
| 1 (1) | 17-1E | GSSFSSYTMG | AIRWSGESPYYADSVKG | RLVPPGIPIERSLENMNYW |
| 2 (2) | 17-2B | GRSFSSYTMG | VIRWSGESPYYADSVKG | RLVPPGIPIERTLESMNYW |
| 3 (3) | 17-3D | GSSFSSYTMG | AIRWSGESPIYADSVKG | RLVPPGIPIERTLESMRYW |
| 4 (4) | 17-4C | GRSFSSYTMG | AIRWSGESPYYADSVKG | RLVPPGIPIERTLESMKDW |
| 5 (5) | 17-7C | GSSFSSYTMG | GIRWSDESPIYADSVKG | RLVPPGIPIPRTSESMRYW |
| 6 (6) | 17-8B | GSSFSSYTMA | AIRWSGESPIYADSVKG | RLVPPGIPIERTLESMRYW |
| 7 (7) | 17-9C | VSSFSSYTMG | GIRWDDENPYYADSVKG | RLVPPGIPFERTLENMRYW |

TABLE 1-continued

VHH number, VHH reference number as used herein, and sequence of CDR1, CDR2 and CDR3 of the various CD1d antibodies of the invention.

| VHH nr (SEQ ID) | VHH ref | CDR1 (SEQ ID 22-42) | CDR2 (SEQ ID 43-63) | CDR3 (SEQ ID 64-84) |
|---|---|---|---|---|
| 8 (8) | 17-10B | GSSFSSYTMG | AIRWDGESPIYAESVKG | RLVPPGIPIERTLESMRYW |
| 9 (9) | 17-11B | GRSFSSYTMG | VIRWSGESPYYADSVKG | RLVPPGIPIERTLESMNYW |
| 10 (10) | 19-12G | GSSFSSYTMG | AIRWSDESPIYAGSVKG | RLVPPGIPIERTLESMRYW |
| 11 (11) | 17-13E | GSSFSSYTMG | AIRWSDESPYYSDSVKG | RLVPPGIPIERTLENMRYS |
| 12 (12) | 18-14B | GSMFSDNVMG | TIRTGGSTNYADSVKG | TIPVPSTPYDYW |
| 13 (13) | 19-15G | GRSFSSYTMG | AIRWSGESPYYADSVKG | RLVPPGIPIERTLENMNYW |
| 14 (14) | 19-22H | GSSFSSYTMG | AIRWSGESPYYADSVKG | RLVPPGIPIERTLESMNYW |
| 18 (15) | 19-21F | GSSFSSYTMG | AIRWSGESPIYADSVKG | RLVPPGIPIERTLESMKDW |
| 19 (16) | 19-23G | GSSFSSYTMT | GIRWSGESPYYADSVKG | RLVPPGIPIERTLESMRYW |
| 20 (17) | 19-24D | GSSFSSYTMG | AIRWSGESPYYGDSVKG | RLVPPGIPIGRTLESMNNW |
| 21 (18) | 19-25F | GSSFSSYTMG | AIRWSGESPYYADSVKG | RLVPPGIPIERALENMNYW |
| 22 (19) | 19-26A | GSSFSSYTMG | AIRWSDESPIYADSVKG | RLVPPGIPIERTLESMRYW |
| 23 (20) | 19-27F | GRSFSSYTMG | AIRWSGESPYYADSVKG | RLVPPGIPIERSLENMNYW |
| 24 (21) | 18-29C | GSIFSINAMG | VISSSGSTNYADSVKG | HVAGFDEYNYW |

TABLE 2

Sequence identity in CDR1, CDR2 and CDR3 compared to 17-1E

| | CDR1 | CDR2 | CDR3 |
|---|---|---|---|
| 17-2B | 90% | 94% | 89% |
| 17-3D | 100% | 94% | 84% |
| 17-4C | 90% | 100% | 79% |
| 17-7C | 100% | 82% | 73% |
| 17-8B | 90% | 94% | 84% |
| 17-9C | 90% | 76% | 84% |
| 17-10B | 100% | 82% | 84% |
| 17-11B | 90% | 94% | 89% |
| 19-12G | 100% | 82% | 84% |
| 17-13E | 100% | 88% | 84% |
| 18-14B | 60% | 64% | 21% |
| 19-15G | 90% | 100% | 95% |
| 19-22H | 100% | 100% | 89% |
| 19-21F | 100% | 94% | 79% |
| 19-23G | 90% | 94% | 84% |
| 19-24D | 100% | 94% | 79% |
| 19-25F | 100% | 100% | 95% |
| 19-26A | 100% | 88% | 84% |
| 19-27F | 90% | 100% | 100% |
| 18-29C | 60% | 64% | 15.7% |

Examples

Immunization

Two individual llamas (*Lama glama*) were immunized as described (Roovers R C et al. Cancer Immunol Immunother. 2007; 56:303-17). Briefly, $10^8$ stable CD1d transduced C1R-cells were injected s.c. on days 0, 14, 28 and 35. For phage display library construction 150 ml blood was collected on day 43.

Selection of CD1d Specific VHH

For construction of a phage display library peripheral blood lymphocytes (PBL) were isolated from the collected 150 ml blood samples. From the isolated lymphocytes, cDNA was prepared and used as template to amplify genes coding for the variable domains of the heavy-chain only antibodies. The PCR fragments were ligated into pUR8100 phagemid vector and transformed in *E. coli* cells. In this way, two VHH libraries were obtained which were subsequently expressed on phages and used for selection. For this purpose, phages from both libraries were incubated for 2 hours at 4° C. with CD1d transfected HeLa-cells. Cells were then washed and bound phages were eluted with 100 mM HCl for 7 minutes at 4° C. Removed phages were then neutralized with Tris-HCl followed by infection into *E. coli*. Selected phages were then counterselected twice for 1 hour at 4° C. using wild type C1R-cells, after which unbound phages were incubated for 1 hour with CD1d transfected C1R-cells. Bound phages were then eluted and infected to *E. coli* as described above. Bacteria were plated on agar plates containing 2% glucose/ampicillin to generate single bacterial colonies coding VHH DNA. VHH DNA from individual clones was digested with Sfi1/BstEII digestion enzymes and cloned into plasmid pMEK219, a derivative from pHen1 (Hoogenboom H R, et al. Nucleic Acids Res 1991; 19:4133-4137). with addition of a HC-V cassette to enable Sfi1/BstEII cloning, and a C-terminal myc- and 6×HIS-tag deletion of the genIII sequence. pMEK219-VHH was transformed to *E. coli* TG1 bacteria.

An overnight culture was used to inoculate 2×TY medium plus 0.1% glucose and 100 ug/ml ampicillin. When OD600 reached IPTG was added to a final concentration of 1 mM. Protein production was allowed for 2-5 hours. Growth of all cultures was performed at 37° C. while vigorously shaking at 200-220 rpm. Protein production was stopped by spinning cultures for 15 minutes at 4° C. The bacterial pellet was resuspended in PBS and frozen for at least 1 hour at −80° C. Bacterial suspension was thawed, slightly shaken for 1 hour at 4° C. and spun at 4500 rpm for 30 minutes. Supernatant was used to confirm binding to CD1d transfected C1R-cells using flowcytometry.

CD1d Specificity of Selected VHH

Confirmation of CD1d specific binding was assessed by flowcytometry using C1R and K562 cells expressing either CD1a, CD1b, CD1c, or CD1d. Staining was performed in a 96-well plate and all incubations were performed in FACS buffer for 30 minutes at 4° C. For initial screenings of binding to CD1d, cells were incubated with 25 µl supernatant containing anti-CD1d VHH. After washing, cells were incubated with anti-myc tag antibody clone 4A6 (Merck Millipore, MA, USA), final dilution 1:500, washed and incubated with goat-anti-mouse F(ab)2 APC (Beckman Coulter, Fullerton, Calif., USA), final dilution 1:200. After a final washing step, VHH binding to cells was assessed by flowcytometry (FACSFortessa, BD Biosciences). VHH showing specific binding were selected. As a positive control the anti-CD1d 51.1 mAb (eBiosciences Inc, New Jersey, USA) was used, as negative control a nanobody specific for azo-dye RR6 was used. Binding of the selected anti-CD1d VHH to CD1d was confirmed after purification (see below) and sequencing of anti-CD1d VHH. For these experiments, anti-CD1d VHH and controls were tested at a concentration of 5 µg/ml. Representative data is shown in FIG. 1.

Fingerprint Analysis and Sequencing

To select structurally different CD1d-specific VHH, DNA from selected VHHs was amplified by colony PCR, digested with Hinfl and subsequently run on a 2% agarose gel. Based on the digestion pattern different families could be selected. Individual families were then sequenced (BaseClear B.V. Leiden, The Netherlands) to confirm unique clones.

VHH Production and Purification

Supernatants containing unique anti-CD1d VHH were produced as described. For purification, these supernatants were subsequently incubated with washed Talon resin (Clontech, Mountain View, Calif., USA) for 1 hour at room temperature. Talon resin was washed 3 times with PBS and once with 15 mM imidazole/PBS pH 7 and eluted with 150 mM imidazole/PBS pH 7. The eluted fraction was dialyzed twice for 24 h against PBS. Concentration of purified VHH was determined by Nanodrop measurement (Thermo Fisher Scientific Inc., Wilmington, Del., USA) and purity was confirmed by coomassie stained protein gel.

Anti-CD1d Mediated moDC Maturation

Immature monocyte derived dendritic cells (moDC) were generated as described (Lameris R. et al, Methods Mol Biol, 2014; 1139: 155-65). moDC were cultured in complete medium (RPM1-1640 containing HEPES, 10% FCS, 0.05 mM beta-mercaptoethanol, (β-ME), 100 IU/mL of sodium penicillin, 100 µg/mL of streptomycin sulfate, and 2.0 mM of l-glutamine) in 48-well plates at a concentration of $6*10^4$ cells/well in the presence of 5 ng/ml rhIL-4, 500 U/ml rhGM-CSF, 1000 U/ml rhINF-γ, 25 µg/ml polymyxin B and 500 nM anti-CD1d VHH or negative control VHH. LPS (200 ng/ml) was used as a positive control. After 24 h supernatants were taken for analysis of IL-12 and 11-10 production (not shown) (using ELISA). After 72 h cells were harvested and analyzed for expression of moDC maturation markers (PE labelled anti-CD86 (not shown), APC labelled anti-CD83, BD Biosciences) using flowcytometry (FACS Fortessa, BD Biosciences). Representative data is shown in FIG. 2.

Inhibition of αGalCer-Induced iNKT Activation by Anti-CD1d VHH iNKT cells were generated as described (Lameris R. et al, Methods Mol Biol 2014; 1139: 155-65). $5*10^4$ CD1d-transfected HeLa cells were cultured overnight at 37° C. in a 96-well plate in DMEM, containing 10% FCS, 0.05 mM β-ME, 100 IU/mL of sodium penicillin, 100 µg/mL of streptomycin sulfate, 2.0 mM of l-glutamine and 400 ng/ml α-GalCer. HeLa-CD1d cells were then washed and incubated with 500 nM anti-CD1d VHH (or negative control VHH) for 2 hours at 37° C. after which $5*10^4$ resting (<25% CD25 expression) iNKT were added. After 24 h, supernatants were harvested for detection of IFN-γ and IL-4 (using ELISA) while iNKT cells were harvested, resuspended in FACS buffer and analyzed by flow-cytometry in order to detect the induction (or inhibition) of iNKT cell activation (assessed by expression of the activation marker CD25 on iNKT cells (FACS Fortessa, BD Biosciences). See FIG. 3 and FIG. 7 for representative results with at least VHH24.

Induction of iNKT Cell Activation by Anti-CD1d VHH iNKT cells were generated as described (Lameris R. et al, Methods Mol Biol 2014; 1139: 155-65). $5*10^4$ CD1d-transfected HeLa cells, CD1d-transfected C1R cells and CD1d-transfected MM.1s cells were cultured overnight at 37° C. in a 96-well plate in DMEM, containing 10% FCS, 0.05 mM β-ME, 100 IU/mL of sodium penicillin, 100 µg/mL of streptomycin sulfate, 2.0 mM of l-glutamine in the presence or absence of 100 ng/ml α-GalCer or vehicle control. CD1d-transfected cells, loaded with α-GalCer or vehicle control, were then washed and incubated with 500 nM anti-CD1d VHH (or negative control VHH) for 2 hours at 37° C. after which $5*10^4$ resting (<25% CD25 expression) iNKT cells were added. After 24 h, supernatants were harvested for detection of IFN-γ and IL-4 (using ELISA) while iNKT cells were harvested, resuspended in FACS buffer and analyzed by flow-cytometry in order to assess the induction of iNKT cell activation (assessed by expression of the activation marker CD25 on iNKT cells (FACS Fortessa, BD Biosciences). See FIG. 4 and FIG. 8 (concentration dependency) for representative results; showing data for VHH12.

Analysis of Annexin V Binding Induced by Anti-CD1d VHH

CD1d-C1R and CD1d-MM.1s (as well as untransfected C1R and MM.1s cell lines as negative controls) were cultured at 37° C. in a 48-well plate at $1*10^5$ cells per well and incubated with 500 nM anti-CD1d VHH, negative control VHH, or anti-CD1d 51.1 mAb (as positive control). After 24 h, cells were stained with annexin V and propidium iodide (P1) according to manufacturers protocol (VPS Diagnostics, Hoeven, the Netherlands) and analyzed by flow cytometry (FACS Fortessa, BD Biosciences). Experimental results are shown in FIG. 5.

Induction of iNKT Cell Activation by Platebound CD1d and Anti-CD1d VHH iNKT cells were generated as described (Lameris R. et al, Methods Mol Biol 2014; 1139: 155-65). α-GalCer (1 mM) or vehicle control (100% DMSO) were heated for 2 minutes at 80° C., sonicated for 5 minutes and subsequently diluted in sterile, warm (37° C.) 0.1% triton-X to a concentration of 100 µM. Next 6 µM of a bispecific construct consisting of an anti-EGFR VHH fused to β2m-human CD1d was added in a 1:1 ratio. Final concentrations of α-GalCer and β2m-CD1d-anti-EGFR construct were 50 µM and 3 µM respectively. Vehicle and α-GalCer where incubated overnight at room temperature while shaking. 96-well plates were coated with anti-flag mAb (Sigma, clone M2; 1:1000) and incubated overnight at 4° C. The next day anti-flag coated plates were washed trice with PBS and incubated with α-GalCer or vehicle loaded construct diluted in PBS (construct concentration 0.5 µM) for 2 hours, while shaking at room temperature. After washing with PBS, coated plates were incubated with 250 nM anti-CD1d VHH for 2 hours at 37° C. after which $1*10^5$ resting (<25% CD25 expression) iNKT cells were added. After 24 h iNKT cells were harvested, resuspended in FACS buffer and analyzed by flow-cytometry in order to assess the induction of iNKT cell activation (assessed by expression of the activation marker CD25 on iNKT cells (FACS Fortessa, BD Biosciences). Results are presented in FIG. 6.

VHH12

In addition to the data shown above, additional experiments were performed using VHH12. The results of the experiments are shown in FIG. 9, FIG. 10 and FIG. 11. FIG. 9 shows induction of iNKT cell degranulation (left) and cytotoxicity against CD1d+ tumor cells line (right). FIG. 10 shows induction of iNKT cell cytotoxicity against CD1d+ primary multiple myeloma cells. FIG. 11 shows induction of iNKT cell cytokine production by anti-CD1d VHH12. For detection of cytokine production HeLa-CD1d cells were pulsed with vehicle control, OCH (a sphingosine truncated derivative of alpha-galactosylceramide (alpha-GC); glycolipid reported to induce Th2-cytokine production in iNKT cells) or αGC, incubated with anti-CD1d VHH and controls and co-cultured with iNKT for 24 h after which supernatants were analyzed (by Cytometric Bead Assay; CBA). N=4; *p<0.05; ****p<0.0001. The anti-CD1d VHH shown is VHH12.

Results

Representative results of the various experiments is shown in the Figures and the accompanying legends; additional experimental data is discussed above in the context of the current invention.

---

The invention claimed is:

1. A compound comprising at least one single-domain antibody which binds to human CD1d, wherein the single-domain antibody comprises complementarity determining regions CDR1, CDR2 and CDR3, wherein CDR1 comprises the amino acid sequence set forth in SEQ ID NO:33, CDR2 comprises the amino acid sequence set forth in SEQ ID NO:54 and CDR3 comprises the amino acid sequence set forth in SEQ ID NO: 75.

2. A compound according to claim 1, wherein the compound comprises the amino acid sequence set forth in SEQ ID NO:12, or a conservative sequence variant thereof.

3. A compound according to claim 1, wherein the compound comprises a label, wherein an pharmaceutical active agent is linked to the compound, wherein the compound is a bivalent or multivalent compound, wherein the compound is fused to an antigen, a peptide or a nucleotide sequence, wherein the compound is a liposome, wherein the compound is a virus, and/or wherein the compound is a nanoparticle.

4. A compound according to claim 1, wherein the compound binds to human CD1d but not to human CD1a, human CD1b and/or human CD1c.

5. A compound according to claim 1, wherein
the compound is capable of inducing activation of CD1d-restricted T cells, including invariant natural killer T-cells, and/or stimulating alpha-galactosyl ceramide, induced activation of CD1d-restricted T cells, including invariant natural killer T-cells.

6. A compound according to claim 1, wherein the compound is a single domain antibody.

7. A compound according to claim 1, wherein the single domain antibody is a humanized single domain antibody.

8. A compound according to claim 1, for use in medical treatment, or for in vivo use as a diagnostic agent.

9. A pharmaceutical composition comprising a compound according to claim 1.

10. A nucleotide sequence that encodes a compound according to claim 1.

11. An isolated host cell or non-human organism comprising a nucleotide sequence encoding a compound according to claim 1.

12. The host cell according to claim 11 that produces said compound or part thereof.

13. A method for preparing a compound comprising at least one single-domain antibody which binds to human CD1d, wherein the method comprises culturing the host cell of claim 12 to express the compound or part thereof; and obtaining the compound.

14. An antibody that comprises a CDR1, CDR2 and CDR3, wherein the CDR1 has the amino acid sequence set forth in SEQ ID NO:33, the CDR2 has the amino acid sequence set forth in SEQ ID NO:54 and CDR3 has the amino acid sequence set forth in SEQ ID NO:75.

15. A compound according to claim 1, wherein the compound comprises the amino acid sequence set forth in SEQ ID NO: 12.

16. A compound according to claim 1, wherein the compound further comprises an additional single domain antibody.

17. A compound according claim 1, wherein the compound is a bispecific or multispecific compound.

18. A compound according claim 1, wherein the compound is linked to another antibody.

* * * * *

SEQUENCE LISTING

```
<160> NUMBER OF SEQ ID NOS: 84

<210> SEQ ID NO 1
<211> LENGTH: 126
<212> TYPE: PRT
<213> ORGANISM: Artificial Sequence
<220> FEATURE:
<223> OTHER INFORMATION: Synthetic

<400> SEQUENCE: 1

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
            20                  25                  30

Met Gly Trp Phe Arg Gln Ala Pro Gly Lys Glu Arg Glu Ile Val Ala
        35                  40                  45

Ala Ile Arg Trp Ser Gly Glu Ser Pro Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Phe Cys Ala
                85                  90                  95

Ala Arg Leu Val Pro Pro Gly Ile Pro Ile Glu Arg Ser Leu Glu Asn
            100                 105                 110

Met Asn Tyr Trp Gly Lys Gly Thr Leu Val Thr Val Ser Ser
        115                 120                 125

<210> SEQ ID NO 2
<211> LENGTH: 126
<212> TYPE: PRT
<213> ORGANISM: Artificial Sequence
<220> FEATURE:
<223> OTHER INFORMATION: Synthetic

<400> SEQUENCE: 2

Val Gln Leu Val Glu Ser Gly Gly Gly Ser Val Gln Ala Gly Gly Ser
1               5                   10                  15

Leu Arg Leu Ser Cys Ala Ala Ser Gly Arg Ser Phe Ser Ser Tyr Thr
            20                  25                  30

Met Gly Trp Cys Arg Gln Ala Pro Gly Lys Glu Arg Glu Cys Val Ala
        35                  40                  45

Val Ile Arg Trp Ser Gly Glu Ser Pro Tyr Tyr Ala Asp Ser Val Lys
    50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Arg Leu Val Pro Pro Gly Ile Pro Ile Glu Arg Thr Leu Glu Ser
            100                 105                 110

Met Asn Tyr Trp Gly Lys Gly Thr Leu Val Thr Val Ser Ser
            115                 120                 125
```

<210> SEQ ID NO 3
<211> LENGTH: 127
<212> TYPE: PRT
<213> ORGANISM: Artificial Sequence
<220> FEATURE:
<223> OTHER INFORMATION: Synthetic

<400> SEQUENCE: 3

```
Gln Val Gln Leu Val Glu Ser Gly Gly Gly Leu Val Gln Ala Gly Gly
  1               5                  10                  15

Ser Leu Arg Leu Ser Cys Ala Ala Ser Gly Ser Ser Phe Ser Ser Tyr
             20                  25                  30

Thr Met Gly Trp Phe Arg Gln Ala Pro Gly Lys Glu Arg Glu Ile Val
         35                  40                  45

Ala Ala Ile Arg Trp Ser Gly Glu Ser Pro Ile Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Leu Val Pro Pro Gly Ile Pro Ile Glu Arg Thr Leu Glu
            100                 105                 110

Ser Met Arg Tyr Trp Gly Lys Gly Thr Leu Val Thr Val Ser Ser
            115                 120                 125
```

<210> SEQ ID NO 4
<211> LENGTH: 130
<212> TYPE: PRT
<213> ORGANISM: Artificial Sequence
<220> FEATURE:
<223> OTHER INFORMATION: Synthetic

<400> SEQUENCE: 4

```
Glu Val Gln Leu Val Glu Ser Gly Gly Gly Leu Val Gln Ala Gly Gly
  1               5                  10                  15

Ser Leu Gly Leu Ser Cys Ala Ala Ser Gly Arg Ser Phe Ser Ser Tyr
             20                  25                  30

Thr Met Gly Val Ile Arg Trp Ser Gly Glu Ser Pro Tyr Ala Asp
         35                  40                  45

Ser Val Lys Gly Ala Ile Arg Trp Ser Gly Glu Ser Pro Tyr Tyr Ala
             50                  55                  60

Asp Ser Val Lys Gly Arg Phe Thr Ile Ser Arg Asp Asn Ala Lys Asn
 65                  70                  75                  80

Thr Leu Tyr Leu Gln Met Asn Asn Leu Lys Pro Glu Asp Thr Ala Val
                 85                  90                  95

Tyr Tyr Cys Ala Ala Arg Leu Val Pro Pro Gly Ile Pro Ile Glu Arg
            100                 105                 110

Thr Leu Glu Ser Met Lys Asp Trp Gly Lys Gly Thr Leu Val Thr Val
            115                 120                 125
```

Ser Ser
    130

<210> SEQ ID NO 5
<211> LENGTH: 129
<212> TYPE: PRT
<213> ORGANISM: Artificial Sequence
<220> FEATURE:
<223> OTHER INFORMATION: Synthetic

<400> SEQUENCE: 5

Val Gln Leu Val Glu Ser Gly Gly Leu Val Gln Ala Gly Gly Ser
1               5                   10                  15

Leu Arg Leu Ser Cys Ala Ala Ser Gly Ser Ser Phe Ser Ser Tyr Thr
                20                  25                  30

Met Gly Ala Ile Arg Trp Ser Asp Glu Ser Pro Ile Tyr Ala Gly Ser
            35                  40                  45

Val Lys Gly Gly Ile Arg Trp Ser Asp Glu Ser Pro Ile Tyr Ala Asp
50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ala Ala Arg Leu Val Pro Pro Gly Ile Pro Ile Pro Arg Thr
            100                 105                 110

Ser Glu Ser Met Arg Tyr Trp Gly Lys Gly Thr Leu Val Thr Val Ser
        115                 120                 125

Ser

<210> SEQ ID NO 6
<211> LENGTH: 130
<212> TYPE: PRT
<213> ORGANISM: Artificial Sequence
<220> FEATURE:
<223> OTHER INFORMATION: Synthetic

<400> SEQUENCE: 6

Gln Val Gln Leu Val Glu Ser Gly Gly Gly Leu Val Gln Ala Gly Asp
1               5                   10                  15

Ser Leu Arg Leu Ser Cys Ala Ala Ser Gly Ser Ser Phe Ser Ser Tyr
                20                  25                  30

Thr Met Ala Ala Ile Arg Trp Ser Asp Glu Ser Pro Tyr Tyr Ser Asp
            35                  40                  45

Ser Val Lys Gly Ala Ile Arg Trp Ser Gly Glu Ser Pro Ile Tyr Ala
50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Asn Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
        115                 120                 125

Ser Ser
    130

<210> SEQ ID NO 7

<211> LENGTH: 129
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Val Ser Ser Phe Ser Ser Tyr
            20                  25                  30

Thr Met Gly Thr Ile Arg Thr Gly Ser Thr Asn Tyr Ala Asp Ser
        35                  40                  45

Val Lys Gly Gly Ile Arg Trp Asp Asp Glu Asn Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Asn Tyr
                85                  90                  95

Tyr Cys Ala Ala Arg Leu Val Pro Pro Gly Ile Pro Phe Glu Arg Thr
            100                 105                 110

Leu Glu Asn Met Arg Tyr Trp Gly Lys Gly Thr Leu Val Thr Val Ser
        115                 120                 125

Ser

<210> SEQ ID NO 8
<211> LENGTH: 130
<212> TYPE: PRT
<213> ORGANISM: Artificial Sequence
<220> FEATURE:
<223> OTHER INFORMATION: Synthetic

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Ala Ile Arg Trp Asp Gly Ser Pro Ile Tyr Ala
    50                  55                  60

Glu Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
        115                 120                 125

Ser Ser
    130

<210> SEQ ID NO 9
<211> LENGTH: 130
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Val Ile Arg Trp Ser Gly Ser Pro Tyr Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Ala Ser Leu Lys Pro Asp Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Asn Tyr Trp Gly Lys Gly Thr Leu Val Thr Val
            115                 120                 125

Ser Ser
    130

<210> SEQ ID NO 10
<211> LENGTH: 130
<212> TYPE: PRT
<213> ORGANISM: Artificial Sequence
<220> FEATURE:
<223> OTHER INFORMATION: Synthetic

<400> SEQUENCE: 10

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Ala Ile Arg Trp Ser Asp Glu Ser Pro Ile Tyr Ala
    50                  55                  60

Gly Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
            115                 120                 125

Ser Ser
    130

<210> SEQ ID NO 11
<211> LENGTH: 129
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ser Ile Asn Asn Gly Ser Thr Lys Tyr Ala Asp Ser
        35                  40                  45

Val Lys Gly Ala Ile Arg Trp Ser Asp Glu Ser Pro Tyr Tyr Ser Asp
 50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ser Ala Arg Leu Val Pro Pro Gly Ile Pro Ile Glu Arg Thr
            100                 105                 110

Leu Glu Asn Met Arg Tyr Ser Gly Lys Gly Thr Leu Val Thr Val Ser
        115                 120                 125

Ser

<210> SEQ ID NO 12
<211> LENGTH: 122
<212> TYPE: PRT
<213> ORGANISM: Artificial Sequence
<220> FEATURE:
<223> OTHER INFORMATION: Synthetic

<400> SEQUENCE: 12

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Met Phe Ser Asp Asn
            20                  25                  30

Val Met Gly Ala Ile Arg Trp Ser Gly Glu Ser Pro Tyr Tyr Val Asp
        35                  40                  45

Ser Val Lys Gly Thr Ile Arg Thr Gly Gly Ser Thr Asn Tyr Ala Asp
 50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Arg His Thr Ile Pro Val Pro Ser Thr Pro Tyr Asp Tyr Trp
            100                 105                 110

Gly Gln Gly Thr Gln Val Thr Val Ser Ser
        115                 120

<210> SEQ ID NO 13
<211> LENGTH: 130
<212> TYPE: PRT
<213> ORGANISM: Artificial Sequence
<220> FEATURE:
<223> OTHER INFORMATION: Synthetic

<400> SEQUENCE: 13

Gln Val Gln Leu Val Glu Ser Gly Gly Gly Leu Val Gln Ala Gly Gly
1               5                   10                  15

Ser Leu Gly Leu Ser Cys Ala Ala Ser Gly Arg Ser Phe Ser Ser Tyr
            20                  25                  30

Thr Met Gly Ala Ile Arg Trp Ser Gly Glu Ser Pro Ile Tyr Ala Asp
        35                  40                  45

Ser Val Lys Gly Ala Ile Arg Trp Ser Gly Glu Ser Pro Tyr Tyr Ala
 50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
            85                  90                  95

Tyr Tyr Cys Ala Ala Arg Leu Val Pro Pro Gly Ile Pro Ile Glu Arg
        100                 105                 110

Thr Leu Glu Asn Met Asn Tyr Trp Gly Lys Gly Thr Leu Val Thr Val
        115                 120                 125

Ser Ser
130

<210> SEQ ID NO 14
<211> LENGTH: 129
<212> TYPE: PRT
<213> ORGANISM: Artificial Sequence
<220> FEATURE:
<223> OTHER INFORMATION: Synthetic

<400> SEQUENCE: 14

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
            20                  25                  30

Met Gly Gly Ile Arg Trp Ser Gly Glu Ser Pro Tyr Tyr Ala Asp Ser
        35                  40                  45

Val Lys Gly Ala Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
            85                  90                  95

Tyr Cys Ala Ala Arg Leu Val Pro Pro Gly Ile Pro Ile Glu Arg Thr
        100                 105                 110

Leu Glu Ser Met Asn Tyr Trp Gly Lys Gly Thr Leu Val Thr Val Ser
        115                 120                 125

Ser

<210> SEQ ID NO 15
<211> LENGTH: 130
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Ala Ile Arg Trp Ser Gly Glu Ser Pro Ile Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
            85                  90                  95

Tyr Tyr Cys Ala Ala Arg Leu Val Pro Pro Gly Ile Pro Ile Glu Arg
                100                 105                 110

Thr Leu Glu Ser Met Lys Asp Trp Gly Lys Gly Thr Leu Val Thr Val
            115                 120                 125

Ser Ser
    130

<210> SEQ ID NO 16
<211> LENGTH: 129
<212> TYPE: PRT
<213> ORGANISM: Artificial Sequence
<220> FEATURE:
<223> OTHER INFORMATION: Synthetic

<400> SEQUENCE: 16

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Thr Val Ile Ser Ser Gly Ser Thr Asn Tyr Ala Asp Ser
        35                  40                  45

Val Lys Gly Gly Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ala Ala Arg Leu Val Pro Pro Gly Ile Pro Ile Glu Arg Thr
                100                 105                 110

Leu Glu Ser Met Arg Tyr Trp Gly Lys Gly Thr Leu Val Thr Val Ser
            115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: Synthetic

<400> SEQUENCE: 17

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
            20                  25                  30

Met Gly Val Ile Arg Trp Ser Gly Glu Ser Pro Tyr Tyr Ala Asp Ser
        35                  40                  45

Val Lys Gly Ala Ile Arg Trp Ser Gly Glu Ser Pro Tyr Tyr Gly Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ala Ala Arg Leu Val Pro Pro Gly Ile Pro Ile Gly Arg Thr
                100                 105                 110

Leu Glu Ser Met Asn Asn Trp Gly Lys Gly Thr Leu Val Thr Val Ser
            115                 120                 125

Ser

<210> SEQ ID NO 18
<211> LENGTH: 130
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Asp Glu Ser Pro Ile Tyr Ala Gly
        35                  40                  45

Ser Val Lys Gly Ala Ile Arg Trp Ser Gly Glu Ser Pro Tyr Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met His Ser Leu Lys Pro Glu Asp Thr Ala Val
            85                  90                  95

Tyr Tyr Cys Ala Ala Arg Leu Val Pro Pro Gly Ile Pro Ile Glu Arg
        100                 105                 110

Ala Leu Glu Asn Met Asn Tyr Trp Gly Lys Gly Thr Leu Val Thr Val
    115                 120                 125

Ser Ser
    130
```

<210> SEQ ID NO 19
<211> LENGTH: 130
<212> TYPE: PRT
<213> ORGANISM: Artificial Sequence
<220> FEATURE:
<223> OTHER INFORMATION: Synthetic

<400> SEQUENCE: 19

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Asp Glu Ser Pro Tyr Tyr Ser Asp
        35                  40                  45

Ser Val Lys Gly Ala Ile Arg Trp Ser Asp Glu Ser Pro Ile Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met His Ser Leu Lys Pro Glu Asp Thr Ala Phe
            85                  90                  95

Tyr Tyr Cys Ala Ala Arg Leu Val Pro Pro Gly Ile Pro Ile Glu Arg
        100                 105                 110

Thr Leu Glu Ser Met Arg Tyr Trp Gly Lys Gly Thr Leu Val Thr Val
    115                 120                 125

Ser Ser
    130
```

<210> SEQ ID NO 20
<211> LENGTH: 129

<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Thr Met Gly Thr Ile Arg Thr Gly Gly Ser Thr Asn Tyr Ala Asp Ser
        35                  40                  45

Val Lys Gly Ala Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Asn Tyr Leu Gln Met Asn Ser Leu Lys Pro Glu Leu Thr Ala Val Tyr
                85                  90                  95

Tyr Cys Ala Ala Arg Leu Val Pro Pro Gly Ile Pro Ile Glu Arg Ser
            100                 105                 110

Leu Glu Asn Met Asn Tyr Trp Gly Lys Gly Thr Leu Val Thr Val Ser
        115                 120                 125

Ser

<210> SEQ ID NO 21
<211> LENGTH: 121
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Ala Ile Arg Trp Ser Gly Glu Ser Pro Tyr Tyr Ala Asp
        35                  40                  45

Ser Val Lys Gly Val Ile Ser Ser Ser Gly Ser Thr Asn Tyr Ala Asp
    50                  55                  60

Ser Val Lys Gly Arg Phe Thr Ile Ser Arg Asp Asn Ala Lys Asn Thr
65                  70                  75                  80

Ala Tyr Leu Gln Met Asn Ser Leu Lys Val Glu Asp Thr Ala Val Tyr
                85                  90                  95

Tyr Cys Ala Ala His Val Ala Gly Phe Asp Glu Tyr Asn Tyr Trp Gly
            100                 105                 110

Gln Gly Thr Gln Val Thr Val Ser Ser
        115                 120

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Ser Ser Phe Ser Ser Tyr Thr Met Gly
1               5                   10

```
<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Gly Arg Ser Phe Ser Ser Tyr Thr Met Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gly Ser Ser Phe Ser Ser Tyr Thr Met Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Gly Arg Ser Phe Ser Ser Tyr Thr Met Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Gly Ser Ser Phe Ser Ser Tyr Thr Met Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic

<400> SEQUENCE: 27

Gly Ser Ser Phe Ser Ser Tyr Thr Met Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Val Ser Ser Phe Ser Ser Tyr Thr Met Gly
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Gly Ser Ser Phe Ser Ser Tyr Thr Met Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

Gly Arg Ser Phe Ser Ser Tyr Thr Met Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Gly Ser Ser Phe Ser Ser Tyr Thr Met Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gly Ser Ser Phe Ser Ser Tyr Thr Met Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

Gly Ser Met Phe Ser Asp Asn Val Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic

<400> SEQUENCE: 34

Gly Arg Ser Phe Ser Ser Tyr Thr Met Gly
1               5                   10

```
<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Gly Ser Ser Phe Ser Ser Tyr Thr Met Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Gly Ser Ser Phe Ser Ser Tyr Thr Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Gly Ser Ser Phe Ser Ser Tyr Thr Met Thr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Gly Ser Ser Phe Ser Ser Tyr Thr Met Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Gly Ser Ser Phe Ser Ser Tyr Thr Met Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Gly Ser Ser Phe Ser Ser Tyr Thr Met Gly
1               5                   10

<210> SEQ ID NO 41
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 41

Gly Arg Ser Phe Ser Ser Tyr Thr Met Gly
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic

<400> SEQUENCE: 42

Gly Ser Ile Phe Ser Ile Asn Ala Met Gly
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Ala Ile Arg Trp Ser Gly Glu Ser Pro Tyr Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Val Ile Arg Trp Ser Gly Glu Ser Pro Tyr Tyr Ala Asp Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Ala Ile Arg Trp Ser Gly Glu Ser Pro Ile Tyr Ala Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46
```

Ala Ile Arg Trp Ser Gly Glu Ser Pro Tyr Tyr Ala Asp Ser Val Lys
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Gly Ile Arg Trp Ser Asp Glu Ser Pro Ile Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ala Ile Arg Trp Ser Gly Glu Ser Pro Ile Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Gly Ile Arg Trp Asp Asp Glu Asn Pro Tyr Tyr Ala Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Ala Ile Arg Trp Asp Gly Glu Ser Pro Ile Tyr Ala Glu Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Val Ile Arg Trp Ser Gly Glu Ser Pro Tyr Tyr Ala Asp Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Synthetic

<400> SEQUENCE: 52

Ala Ile Arg Trp Ser Asp Glu Ser Pro Ile Tyr Ala Gly Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Ala Ile Arg Trp Ser Asp Glu Ser Pro Tyr Tyr Ser Asp Ser Val Lys
1               5                   10                  15

Gly

<210> SEQ ID NO 54
<211> LENGTH: 16
<212> TYPE: PRT
<213> ORGANISM: Artificial Sequence
<220> FEATURE:
<223> OTHER INFORMATION: Synthetic

<400> SEQUENCE: 54

Thr Ile Arg Thr Gly Gly Ser Thr Asn Tyr Ala Asp Ser Val Lys Gly
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: Synthetic

<400> SEQUENCE: 55

Ala Ile Arg Trp Ser Gly Glu Ser Pro Tyr Tyr Ala Asp Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Ala Ile Arg Trp Ser Gly Glu Ser Pro Tyr Tyr Ala Asp Ser Val Lys
1               5                   10                  15

Gly

<210> SEQ ID NO 57
<211> LENGTH: 17
<212> TYPE: PRT
<213> ORGANISM: Artificial Sequence

```
<220> FEATURE:
<223> OTHER INFORMATION: Synthetic

<400> SEQUENCE: 57

Ala Ile Arg Trp Ser Gly Glu Ser Pro Ile Tyr Ala Asp Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Synthetic

<400> SEQUENCE: 58

Gly Ile Arg Trp Ser Gly Glu Ser Pro Tyr Tyr Ala Asp Ser Val Lys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic

<400> SEQUENCE: 59

Ala Ile Arg Trp Ser Gly Glu Ser Pro Tyr Tyr Gly Asp Ser Val Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

Ala Ile Arg Trp Ser Gly Glu Ser Pro Tyr Tyr Ala Asp Ser Val Lys
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

Ala Ile Arg Trp Ser Asp Glu Ser Pro Ile Tyr Ala Asp Ser Val Lys
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: Synthetic

<400> SEQUENCE: 62
```

```
Ala Ile Arg Trp Ser Gly Glu Ser Pro Tyr Tyr Ala Asp Ser Val Lys
1               5                   10                  15

Gly

<210> SEQ ID NO 63
<211> LENGTH: 16
<212> TYPE: PRT
<213> ORGANISM: Artificial Sequence
<220> FEATURE:
<223> OTHER INFORMATION: Synthetic

<400> SEQUENCE: 63

Val Ile Ser Ser Ser Gly Ser Thr Asn Tyr Ala Asp Ser Val Lys Gly
1               5                   10                  15

<210> SEQ ID NO 64
<211> LENGTH: 19
<212> TYPE: PRT
<213> ORGANISM: Artificial Sequence
<220> FEATURE:
<223> OTHER INFORMATION: Synthetic

<400> SEQUENCE: 64

Arg Leu Val Pro Pro Gly Ile Pro Ile Glu Arg Ser Leu Glu Asn Met
1               5                   10                  15

Asn Tyr Trp

<210> SEQ ID NO 65
<211> LENGTH: 19
<212> TYPE: PRT
<213> ORGANISM: Artificial Sequence
<220> FEATURE:
<223> OTHER INFORMATION: Synthetic

<400> SEQUENCE: 65

Arg Leu Val Pro Pro Gly Ile Pro Ile Glu Arg Thr Leu Glu Ser Met
1               5                   10                  15

Asn Tyr Trp

<210> SEQ ID NO 66
<211> LENGTH: 19
<212> TYPE: PRT
<213> ORGANISM: Artificial Sequence
<220> FEATURE:
<223> OTHER INFORMATION: Synthetic

<400> SEQUENCE: 66

Arg Leu Val Pro Pro Gly Ile Pro Ile Glu Arg Thr Leu Glu Ser Met
1               5                   10                  15

Arg Tyr Trp

<210> SEQ ID NO 67
<211> LENGTH: 19
<212> TYPE: PRT
<213> ORGANISM: Artificial Sequence
<220> FEATURE:
<223> OTHER INFORMATION: Synthetic

<400> SEQUENCE: 67

Arg Leu Val Pro Pro Gly Ile Pro Ile Glu Arg Thr Leu Glu Ser Met
1               5                   10                  15

Lys Asp Trp
```

<210> SEQ ID NO 68
<211> LENGTH: 19
<212> TYPE: PRT
<213> ORGANISM: Artificial Sequence
<220> FEATURE:
<223> OTHER INFORMATION: Synthetic

<400> SEQUENCE: 68

Arg Leu Val Pro Pro Gly Ile Pro Ile Pro Arg Thr Ser Glu Ser Met
1               5                   10                  15

Arg Tyr Trp

<210> SEQ ID NO 69
<211> LENGTH: 19
<212> TYPE: PRT
<213> ORGANISM: Artificial Sequence
<220> FEATURE:
<223> OTHER INFORMATION: Synthetic

<400> SEQUENCE: 69

Arg Leu Val Pro Pro Gly Ile Pro Ile Glu Arg Thr Leu Glu Ser Met
1               5                   10                  15

Arg Tyr Trp

<210> SEQ ID NO 70
<211> LENGTH: 19
<212> TYPE: PRT
<213> ORGANISM: Artificial Sequence
<220> FEATURE:
<223> OTHER INFORMATION: Synthetic

<400> SEQUENCE: 70

Arg Leu Val Pro Pro Gly Ile Pro Phe Glu Arg Thr Leu Glu Asn Met
1               5                   10                  15

Arg Tyr Trp

<210> SEQ ID NO 71
<211> LENGTH: 19
<212> TYPE: PRT
<213> ORGANISM: Artificial Sequence
<220> FEATURE:
<223> OTHER INFORMATION: Synthetic

<400> SEQUENCE: 71

Arg Leu Val Pro Pro Gly Ile Pro Ile Glu Arg Thr Leu Glu Ser Met
1               5                   10                  15

Arg Tyr Trp

<210> SEQ ID NO 72
<211> LENGTH: 19
<212> TYPE: PRT
<213> ORGANISM: Artificial Sequence
<220> FEATURE:
<223> OTHER INFORMATION: Synthetic

<400> SEQUENCE: 72

Arg Leu Val Pro Pro Gly Ile Pro Ile Glu Arg Thr Leu Glu Ser Met
1               5                   10                  15

Asn Tyr Trp

<210> SEQ ID NO 73
<211> LENGTH: 19
<212> TYPE: PRT

```
<213> ORGANISM: Artificial Sequence
<220> FEATURE:
<223> OTHER INFORMATION: Synthetic

<400> SEQUENCE: 73

Arg Leu Val Pro Pro Gly Ile Pro Ile Glu Arg Thr Leu Glu Ser Met
1               5                   10                  15

Arg Tyr Trp

<210> SEQ ID NO 74
<211> LENGTH: 19
<212> TYPE: PRT
<213> ORGANISM: Artificial Sequence
<220> FEATURE:
<223> OTHER INFORMATION: Synthetic

<400> SEQUENCE: 74

Arg Leu Val Pro Pro Gly Ile Pro Ile Glu Arg Thr Leu Glu Asn Met
1               5                   10                  15

Arg Tyr Ser

<210> SEQ ID NO 75
<211> LENGTH: 12
<212> TYPE: PRT
<213> ORGANISM: Artificial Sequence
<220> FEATURE:
<223> OTHER INFORMATION: 3

<400> SEQUENCE: 75

Thr Ile Pro Val Pro Ser Thr Pro Tyr Asp Tyr Trp
1               5                   10

<210> SEQ ID NO 76
<211> LENGTH: 19
<212> TYPE: PRT
<213> ORGANISM: Artificial Sequence
<220> FEATURE:
<223> OTHER INFORMATION: Synthetic

<400> SEQUENCE: 76

Arg Leu Val Pro Pro Gly Ile Pro Ile Glu Arg Thr Leu Glu Asn Met
1               5                   10                  15

Asn Tyr Trp

<210> SEQ ID NO 77
<211> LENGTH: 19
<212> TYPE: PRT
<213> ORGANISM: Artificial Sequence
<220> FEATURE:
<223> OTHER INFORMATION: Synthetic

<400> SEQUENCE: 77

Arg Leu Val Pro Pro Gly Ile Pro Ile Glu Arg Thr Leu Glu Ser Met
1               5                   10                  15

Asn Tyr Trp

<210> SEQ ID NO 78
<211> LENGTH: 19
<212> TYPE: PRT
<213> ORGANISM: Artificial Sequence
<220> FEATURE:
<223> OTHER INFORMATION: Synthetic

<400> SEQUENCE: 78
```

```
Arg Leu Val Pro Pro Gly Ile Pro Ile Glu Arg Thr Leu Glu Ser Met
1               5                   10                  15

Lys Asp Trp

<210> SEQ ID NO 79
<211> LENGTH: 19
<212> TYPE: PRT
<213> ORGANISM: Artificial Sequence
<220> FEATURE:
<223> OTHER INFORMATION: Synthetic

<400> SEQUENCE: 79

Arg Leu Val Pro Pro Gly Ile Pro Ile Glu Arg Thr Leu Glu Ser Met
1               5                   10                  15

Arg Tyr Trp

<210> SEQ ID NO 80
<211> LENGTH: 19
<212> TYPE: PRT
<213> ORGANISM: Artificial Sequence
<220> FEATURE:
<223> OTHER INFORMATION: Synthetic

<400> SEQUENCE: 80

Arg Leu Val Pro Pro Gly Ile Pro Ile Gly Arg Thr Leu Glu Ser Met
1               5                   10                  15

Asn Asn Trp

<210> SEQ ID NO 81
<211> LENGTH: 19
<212> TYPE: PRT
<213> ORGANISM: Artificial Sequence
<220> FEATURE:
<223> OTHER INFORMATION: Synthetic

<400> SEQUENCE: 81

Arg Leu Val Pro Pro Gly Ile Pro Ile Glu Arg Ala Leu Glu Asn Met
1               5                   10                  15

Asn Tyr Trp

<210> SEQ ID NO 82
<211> LENGTH: 19
<212> TYPE: PRT
<213> ORGANISM: Artificial Sequence
<220> FEATURE:
<223> OTHER INFORMATION: Synthetic

<400> SEQUENCE: 82

Arg Leu Val Pro Pro Gly Ile Pro Ile Glu Arg Thr Leu Glu Ser Met
1               5                   10                  15

Arg Tyr Trp

<210> SEQ ID NO 83
<211> LENGTH: 19
<212> TYPE: PRT
<213> ORGANISM: Artificial Sequence
<220> FEATURE:
<223> OTHER INFORMATION: Synthetic

<400> SEQUENCE: 83

Arg Leu Val Pro Pro Gly Ile Pro Ile Glu Arg Ser Leu Glu Asn Met
1               5                   10                  15

Asn Tyr Trp
```

```
<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

His Val Ala Gly Phe Asp Glu Tyr Asn Tyr Trp
1               5                   10
```